United States Patent
Tang et al.

(10) Patent No.: US 10,194,901 B2
(45) Date of Patent: *Feb. 5, 2019

(54) SYSTEMS AND METHODS FOR SUTURE DELIVERY

(71) Applicant: Terumo Medical Corporation, Somerset, NJ (US)

(72) Inventors: Hsiao-Wei Tang, Taipei (TW); Yu-Shih Weng, Taipei (TW); Shih-Jui Han, Taipei (TW); Chung-Chu Chen, Taipei (TW); Shih-Ming Wang, Taipei (TW); Chun-Chia Juan, Taipei (TW)

(73) Assignee: Terumo Medical Corporation, Somerset, NJ (US)

( * ) Notice: Subject to any disclaimer, the term of this patent is extended or adjusted under 35 U.S.C. 154(b) by 460 days.

This patent is subject to a terminal disclaimer.

(21) Appl. No.: 14/726,963

(22) Filed: Jun. 1, 2015

(65) Prior Publication Data
US 2015/0257753 A1 Sep. 17, 2015

Related U.S. Application Data

(63) Continuation-in-part of application No. 14/186,246, filed on Feb. 21, 2014, now Pat. No. 9,668,724.
(Continued)

(51) Int. Cl.
*A61B 17/04* (2006.01)
*A61B 17/062* (2006.01)
(Continued)

(52) U.S. Cl.
CPC ...... *A61B 17/0469* (2013.01); *A61B 17/0057* (2013.01); *A61B 17/0625* (2013.01);
(Continued)

(58) Field of Classification Search
CPC . A61B 17/0057; A61B 17/04–17/0485; A61B 2017/00575–2017/00676; A61B 2017/0403–2017/048
See application file for complete search history.

(56) References Cited

U.S. PATENT DOCUMENTS

| | | | |
|---|---|---|---|
| 5,320,632 A | 6/1994 | Heidmueller | |
| 5,964,773 A | 10/1999 | Greenstein | |

(Continued)

FOREIGN PATENT DOCUMENTS

| | | |
|---|---|---|
| EP | 0647430 A2 | 4/1995 |
| JP | 2001522269 | 11/2001 |

(Continued)

OTHER PUBLICATIONS

Notification of Reasons for Refusal issued in Japan Application No. 2015559021, dated Sep. 5, 2017.

(Continued)

*Primary Examiner* — Darwin Erezo
*Assistant Examiner* — Jonathan Hollm
(74) *Attorney, Agent, or Firm* — Dergosits & Noah LLP; Todd A. Noah

(57) ABSTRACT

Systems and methods are provided for suturing tissue. An elongated deployment shaft carries a needle deployment assembly with needles carrying suture material and a stabilizer that is reconfigurable between an unexpanded insertion profile and an expanded profile. A catcher tube over the shaft having a catcher at a distal end may retain at least a portion of the needles carrying the suture material when the needles are passed through the tissue to be sutured into engagement with the catcher. A sheath over the catcher tube may sandwich tissue to be sutured against the stabilizer when expanded under control of first actuator. A second actuator may control the needles.

30 Claims, 20 Drawing Sheets

Related U.S. Application Data

(60) Provisional application No. 62/006,709, filed on Jun. 2, 2014.

(51) Int. Cl.
*A61B 17/00* (2006.01)
*A61B 17/06* (2006.01)
*A61B 17/22* (2006.01)
*A61B 17/29* (2006.01)
*A61B 90/00* (2016.01)

(52) U.S. Cl.
CPC .............. *A61B 2017/00663* (2013.01); *A61B 2017/00672* (2013.01); *A61B 2017/00858* (2013.01); *A61B 2017/00986* (2013.01); *A61B 2017/047* (2013.01); *A61B 2017/0472* (2013.01); *A61B 2017/06042* (2013.01); *A61B 2017/22038* (2013.01); *A61B 2017/22069* (2013.01); *A61B 2017/2923* (2013.01); *A61B 2090/0811* (2016.02); *A61B 2218/00* (2013.01)

(56) References Cited

U.S. PATENT DOCUMENTS

| | | | |
|---|---|---|---|
| 6,024,747 A | 2/2000 | Kontos | |
| 6,036,699 A | 3/2000 | Andreas et al. | |
| 6,280,460 B1 | 8/2001 | Bolduc et al. | |
| 6,355,050 B1 | 3/2002 | Andreas et al. | |
| 6,464,707 B1 | 10/2002 | Bjerken | |
| 6,896,685 B1 | 5/2005 | Davenport | |
| 7,879,049 B2 | 2/2011 | Dillon | |
| 2002/0072768 A1* | 6/2002 | Ginn | A61B 17/0057 606/213 |
| 2005/0216037 A1 | 9/2005 | Davenport | |
| 2010/0016810 A1* | 1/2010 | Drews | A61B 17/0057 604/272 |
| 2010/0145364 A1 | 6/2010 | Keren et al. | |
| 2011/0288563 A1 | 11/2011 | Gianotti | |
| 2012/0296347 A1* | 11/2012 | Roorda | A61B 17/0482 606/145 |
| 2012/0296373 A1 | 11/2012 | Roorda et al. | |
| 2013/0165956 A1 | 6/2013 | Sherts et al. | |
| 2013/0178872 A1* | 7/2013 | Shriver | A61B 17/0057 606/148 |

FOREIGN PATENT DOCUMENTS

| | | |
|---|---|---|
| JP | 2002502658 | 1/2002 |
| JP | 2002537887 | 11/2002 |
| JP | 2003509175 | 3/2003 |
| JP | 2003511187 | 3/2003 |
| WO | 2005/112789 A2 | 12/2005 |
| WO | 2005112789 A2 | 12/2005 |
| WO | 07/025302 A3 | 11/2007 |
| WO | 11/112721 A1 | 9/2011 |
| WO | 2011112721 A1 | 9/2011 |

OTHER PUBLICATIONS

Notification of Reason for Refusal, issued for Korea Patent Application No. 10-2016-7036490, dated Jan. 16, 2018.
International Search Report and Written Opinion for International Application No. PCT/IB2015/001590; dated Jan. 21, 2016.
International Preliminary Report on Patentability for International Application No. PCT/IB2015/001590; dated Dec. 6, 2016.
European Search Report from corresponding European Patent Application 17163400.9, dated May 23, 2017, pp. 1-8.
European Search Report and Written Opinion for co-pending European Application No. 17178418.4, dated Oct. 20, 2017.
International Search Report dated May 14, 2014 in corresponding PCT Application No. PCT/US2014/017813.

* cited by examiner

SYSTEMS AND METHODS FOR SUTURE DELIVERY

RELATED APPLICATIONS

This application claims priority to and the benefit of U.S. Provisional Patent Application Ser. No. 62/006,709, filed Jun. 2, 2014 and is a continuation-in-part application of U.S. application Ser. No. 14/186,246, filed Feb. 21, 2014, the contents all of which is incorporated in its entirety herein by reference.

FIELD OF THE PRESENT DISCLOSURE

The present disclosure relates generally to techniques and devices for closing openings in a patient's vasculature or other body lumens. For example, the present disclosure relates to systems, devices, and methods for suturing of arterial and venous puncture sites to approximate tissue around the opening, such as may be required following a surgical procedure.

BACKGROUND

To improve recovery time, a variety of interventional and diagnostic procedures may be carried out in a minimally invasive manner by accessing a desired location within a patient's body. By introducing catheters or other elongated devices into the vasculature at a convenient entry point, such procedures may be performed at a remote location by guiding the device through the body lumen to the desired position. Although these techniques represent less impact on the patient than conventional open procedures, access to the vasculature requires forming an opening in an artery or vein that subsequently must be repaired.

A variety of methods may be used to close the access opening. Conventionally, hemostasis may be achieved through manual compression to substantially reduce the flow of blood through the opening and allow clot formation. Although generally successful, compression may be take a significant amount of time and may be associated with considerable patient discomfort. Additionally, complications such as unintended total occlusion of the lumen that may result in ischemia or thrombosis can occur. These aspects may be exacerbated depending upon the size of the opening necessary to introduce the device, whether anticoagulants are employed and on the condition of the patient.

To ameliorate these problems, techniques for suturing the opening to achieve hemostasis and reduce time to ambulation have been developed. In order to maintain the minimal invasiveness of the procedure, many of these techniques are adapted to be performed. For example, the suture delivering device may be introduced through the same opening used to perform the procedure. Typically, one or more needles are deployed by the suture delivering device to pierce the vessel wall and draw the suture material through so that the suture may be secured over the adventitial surface and close the opening.

Despite the benefits associated with the use of suture delivering devices, a number of challenges exist. In particular, it is desirable for the needle or needles to be positioned accurately with respect to the vessel wall so as to pierce the tissue far enough away from the opening to result in a sufficiently robust location for the suture. It is also desirable to provide a device configured to deploy and actuate the needles in a reproducible manner to minimize the amount of skill required from the operator. Accordingly, this disclosure is directed to systems and methods for suturing an opening in a body lumen while providing these and other desired characteristics.

SUMMARY

This disclosure includes a suture delivery device for suturing tissue. The suture delivery device may include an elongated deployment shaft, a needle deployment assembly carried by the shaft, including a plurality of needles carrying suture material configured to have an insertion profile at a distal position and to deflect radially outwards to a piercing angle when moved proximally relative to the shaft, a stabilizer carried by the shaft at a location proximal of the needle deployment assembly, wherein the stabilizer is reconfigurable between an unexpanded insertion profile and an expanded profile, a catcher tube coaxially and slidably disposed over the shaft having a catcher at a distal end, wherein the catcher is configured to retain at least a portion of each of the plurality of needles carrying the suture material when the needles are passed through the tissue to be sutured to a proximal position that engages the catcher and a sheath coaxially and slidably disposed over the catcher tube, wherein a distal end of the sheath is configured to sandwich tissue to be sutured against the stabilizer when expanded.

In one aspect, the device may have a handle with an actuator to expand the stabilizer. The first actuator may also move the sheath distally relative to the shaft. The first actuator may be a slider moveable from a proximal position to a distal position. The slider may be coupled to proximal ends of the sheath and the catcher tube and a proximal end of the stabilizer may be secured to the catcher tube and a distal end of the stabilizer may be secured to the shaft such that movement of the slider from the proximal position to the distal position moves the catcher tube distally relative to the shaft to decrease a distance between the proximal end of the stabilizer and the distal end of the stabilizer to expand the stabilizer and moves the sheath distally relative to the shaft to sandwich tissue to be sutured between the distal end of the sheath and the expanded stabilizer. Further, the handle may have a stabilizer control to automatically engage when the slider is in the distal position to prevent further relative movement between the catcher tube and the shaft and to prevent further relative movement between the sheath and the shaft. Still further, the handle may have a release trigger to disengage the stabilizer control when the slider is in the distal position and allow further relative movement between the catcher tube and the shaft so that the stabilizer can return to the unexpanded insertion profile.

In one aspect, the stabilizer may have at least one deflectable wings that deflect outwards when a distance between a proximal end of the stabilizer and a distal end of the stabilizer is reduced. The deflectable wings may have an asymmetric configuration when expanded configured to compensate for an insertion angle of the suture delivery device relative to the tissue to be sutured.

In one aspect, the device may have a handle at a proximal end of the shaft with a second actuator to move the needles proximally and distally relative to the shaft. The second actuator has a first range of travel to move the plurality of needles from the distal position to the proximal position. The second actuator may also have a second range of travel to move a portion of each of the plurality of needles not retained by the catcher from the proximal position to the distal position. The second actuator may be a plunger coupled to a plunger rack, and the device may also include a trigger rack and a pinion, wherein the plurality of needles are coupled to the trigger rack by a trigger wire slidably and coaxially disposed within the shaft, such that during the first range of travel, the trigger rack and the plunger rack engage the pinion so that distal movement of the plunger rack causes proximal movement of the trigger wire relative to the shaft. Further, during the second range of travel, the plunger rack may not engage the pinion and directly engage the trigger rack so that distal movement of the plunger rack causes distal movement of the trigger wire relative to the shaft.

The device may also include both first and second actuators. In an embodiment, movement of the second actuator to an end of the second range of travel may disengage the stabilizer control to allow further relative movement between the catcher tube and the shaft so that the stabilizer can return to the unexpanded insertion profile.

In one aspect, each of the plurality of needles may include a needle base and a detachable needle tip that carries the suture material. Each needle tip may engage the catcher when the plurality of needles are moved to the proximal position and the catcher may retain each needle tip when each of the needle bases are returned to the distal position. Each needle base and corresponding needle tip may have a retention force to keep the needle tips in position on the needle bases until moved proximally into engagement with the catcher. The retention force may depend at least in part on a surface treatment, which may be a layer of nitinol oxide.

This disclosure may also include a suture delivery device for suturing tissue having a single actuator. For example the suture delivery device may have an elongated deployment shaft, a needle deployment assembly carried by the shaft, including a plurality of needles carrying suture material configured to have an insertion profile at a distal position and to deflect radially outwards to a piercing angle when moved proximally relative to the shaft and a catcher tube coaxially and slidably disposed over the shaft having a catcher at a distal end, wherein the catcher is configured to retain at least a portion of each of the plurality of needles carrying the suture material when the needles are passed through the tissue to be sutured to a proximal position that engages the catcher. A handle at a proximal end of the shaft may have an actuator configured to move the needles proximally and distally relative to the shaft.

This disclosure also includes methods for delivering a suture. For example, a suitable method may include providing an elongated deployment shaft, a needle deployment assembly carried by the shaft, including a plurality of needles carrying suture material, a stabilizer carried by the shaft at a location proximal of the needle deployment assembly, a catcher tube coaxially and slidably disposed over the shaft having a catcher at a distal end, and a sheath coaxially and slidably disposed over the catcher tube, advancing the elongated deployment shaft to a desired position in a patient, reconfiguring the stabilizer from an unexpanded insertion profile to an expanded profile, sandwiching tissue to be sutured between a distal end of the sheath and the expanded stabilizer, deflecting the plurality of needles radially outwards to a piercing angle from an insertion profile at a distal position with proximal movement relative to the shaft, engaging the catcher with the plurality of needles when moved to a proximal position by passing through the tissue to be sutured, retaining at least a portion of each of the plurality of needles carrying the suture material with the catcher and returning a portion of each of the plurality of needles not retained by the catcher to the insertion profile at the distal position.

In one aspect, reconfiguring the stabilizer and sandwiching the tissue to be sutured may be performed by operating a first actuator. A proximal end of the stabilizer may be secured to the catcher tube and a distal end of the stabilizer may be secured to the shaft, so that operating the first actuator moves the catcher tube distally relative to the shaft to decrease a distance between the proximal end of the stabilizer and the distal end of the stabilizer to expand the stabilizer and moves the sheath distally relative to the shaft.

In one aspect, deflecting the plurality of needles radially outward, engaging the catcher with the plurality of needles and returning a portion of each of the plurality of needles not retained by the catcher to the distal position may be performed by operating a second actuator. Operating the second actuator may include moving the second actuator through a first range of travel to move the plurality of needles from the distal position to the proximal position and moving the second actuator through a second range of travel to move a portion of each of the plurality of needles not retained by the catcher from the proximal position to the distal position.

In yet another aspect, the disclosure includes a method for delivering a suture by providing an elongated deployment shaft, a needle deployment assembly carried by the shaft, including a plurality of needles carrying suture material and a catcher tube coaxially and slidably disposed over the shaft having a catcher at a distal end, advancing the elongated deployment shaft to a desired position in a patient, deflecting the plurality of needles radially outwards to a piercing angle from an insertion profile at a distal position with proximal movement relative to the shaft, engaging the catcher with the plurality of needles when moved to a proximal position by passing through the tissue to be sutured, retaining at least a portion of each of the plurality of needles carrying the suture material with the catcher and returning a portion of each of the plurality of needles not retained by the catcher to the insertion profile at the distal position.

BRIEF DESCRIPTION OF THE DRAWINGS

Further features and advantages will become apparent from the following and more particular description of the preferred embodiments of the disclosure, as illustrated in the accompanying drawings, and in which like referenced characters generally refer to the same parts or elements throughout the views, and in which.

DETAILED DESCRIPTION

Figure 1:
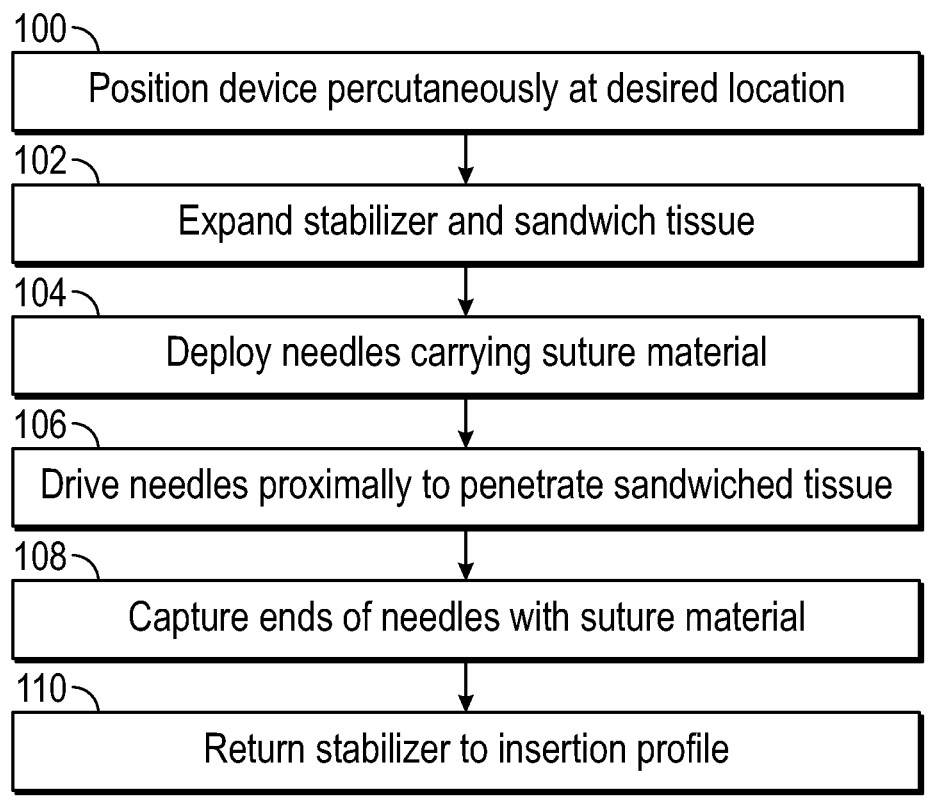
FIG. 1 depicts a flowchart representing a suitable routine for delivery sutures, according to one embodiment.

At the outset, it is to be understood that this disclosure is not limited to particularly exemplified materials, architectures, routines, methods or structures as such may vary. Thus, although a number of such options, similar or equivalent to those described herein, can be used in the practice or embodiments of this disclosure, the preferred materials and methods are described herein.

It is also to be understood that the terminology used herein is for the purpose of describing particular embodiments of this disclosure only and is not intended to be limiting.

The detailed description set forth below in connection with the appended drawings is intended as a description of exemplary embodiments of the present disclosure and is not intended to represent the only exemplary embodiments in which the present disclosure can be practiced. The term "exemplary" used throughout this description means "serving as an example, instance, or illustration," and should not necessarily be construed as preferred or advantageous over other exemplary embodiments. The detailed description includes specific details for the purpose of providing a thorough understanding of the exemplary embodiments of the specification. It will be apparent to those skilled in the art that the exemplary embodiments of the specification may be practiced without these specific details. In some instances, well known structures and devices are shown in block diagram form in order to avoid obscuring the novelty of the exemplary embodiments presented herein.

For purposes of convenience and clarity only, directional terms, such as top, bottom, left, right, up, down, over, above, below, beneath, rear, back, and front, may be used with respect to the accompanying drawings. These and similar directional terms should not be construed to limit the scope of the disclosure in any manner.

Unless defined otherwise, all technical and scientific terms used herein have the same meaning as commonly understood by one having ordinary skill in the art to which the disclosure pertains. For example, the term "suturing" includes drawing two surfaces or edges together with a flexible material to close a puncture, opening, or other wound, wherein the suture is a material that may be synthetic or natural, such as a polymer, gut, metallic wire or other suitable equivalents.

Finally, as used in this specification and the appended claims, the singular forms "a," "an" and "the" include plural referents unless the content clearly dictates otherwise.

According to this disclosure, a device for applying sutures to promote hemostasis following an interventional procedure may be configured to perform a sequence of operations associated with positioning the device in the patient's vasculature, sandwiching tissue using an expanded portion of the device to stabilize the tissue for suture deployment, deploying needles carrying suture material at a piercing angle to pass them through the stabilized tissue and returning the device to an unexpanded condition to release the sandwiched tissue and allow the device to be withdrawn. In particular, as will be described below, aspects of this disclosure details techniques for automating at least some of these operations using actuators that cause the device to perform the operations in a reproducible manner. For example, a first actuator may be employed to expand the a distal portion of the device and sandwich the tissue and a second actuator may be used to deploy needles carrying suture material at a piercing angle and drive them through the sandwiched tissue, to capture the penetrating ends of the needles and to return the distal portion of the device to its unexpanded condition.

Turning now to FIG. 1, an example routine for deploying sutures using a device of this disclosure may therefor include generally begin with 100 to position the device at a desired location, such as by using a bleed back lumen with a port in the distal end of the device so that when the port is located within the vessel, blood will enter the port, flow through the lumen and provide a visual indication at the proximal portion of the device. Following positioning, in 102 soft tissue at the desired suture site is stabilized by expanding a stabilizer on a distal portion of the device and sandwiching the tissue between the stabilizer and a portion of the device that is relatively more proximal. The distal expandable stabilizer exhibits a reduced insertion profile and an expanded profile for stabilizing tissue during delivery of the sutures. Relative movement of the stabilizer may allow tissue to be secured between the stabilizer and the relatively more proximal portion and provide a target for needle-deployed sutures carried by the device. As will be appreciated from the discussions below, the relative movement may involve movement of the stabilizer towards the proximal portion, movement of the proximal portion towards the stabilizer, or both. The sandwiched tissue may include portions of the vessel wall surrounding the puncture being closed.

Next, in 104, a plurality of needles carrying suture material that are disposed distal of the sandwiched tissue are deployed at a piercing angle so that proximal movement of the needles in 106 penetrates the sandwiched tissue. Following penetration of the sandwiched tissue by the needles, at least a portion of the needles are captured proximally in 108. In some embodiments, this may include capturing detachable needle tips that carry the suture material as will be described below. To prepare for withdrawal of the device, in 110 the stabilizer and needle deployment mechanism are returned to their delivery configuration. According to the techniques of this disclosure, it may be desirable to automate some or all of these operations. For example, in an embodiment, a first actuator may be used to perform 102 and a second actuator may be used to perform 104-110. Any suitable actuator configuration, including a push button, slide slider, pull lever and/or push plunger may be employed. Any desired number and sequence of operations may be coordinated and/or automated by linking the operations to a single actuator.

Figure 2:
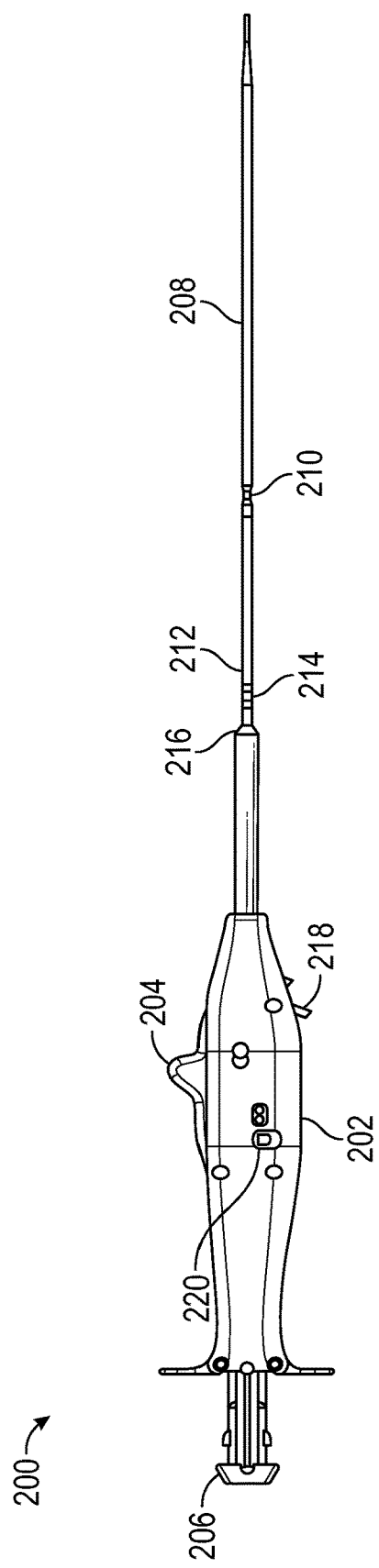
FIG. 2 schematically depicts an overview of a suture delivery device of FIG. 1, according to one embodiment.

To help illustrate aspects of this disclosure, FIG. 2 is a schematic overview of a suture delivering device 200 according to one embodiment. Device 200 includes handle 202 having a first actuator configured as slider 204 and a second actuator configured as plunger 206. The elongated distal portion of device 200 includes catheter 208 for deployment within a patient's vessel. Guidewire exchange port 210 may be used to facilitate advancement of catheter 208 over a guidewire already positioned within the patient's vasculature using known techniques. Proximal to catheter 208 is needle deployment assembly 212 and stabilizer 214. Stabilizer 214 may be reconfigured between the reduced profile shown for insertion and an expanded configuration. While in its expanded configuration, relative movement between the distal end of sheath 216 and stabilizer 214 may be used to sandwich tissue in preparation of suture delivery. In this embodiment, slider 204 may be actuated to expand stabilizer 214 and generate the relative movement between sheath 216 and stabilizer 214. Further, plunger 206 may be actuated so that the plurality of needles within needle deployment assembly 212 are first lifted from their insertion profile to a piercing angle and then driven to penetrate the tissue sandwiched between stabilizer 214 and sheath 216. Continued actuation of plunger 206 may cause at least a portion of the needles to be captured within sheath 216. Subsequently, stabilizer 214 and needle deployment assembly 212 are returned to their insertion profile to facilitate withdrawal of device 200. As shown, device 200 may include a bleed back indicator 218 on handle 202 which is in communication with a port positioned adjacent stabilizer 214 to provide visual feedback in the form of blood flow when stabilizer 214 is positioned within the patient's vessel. Additionally, device 200 may include release trigger 220 to return stabilizer 214 to its insertion profile without actuating plunger 206 and performing the associated operations if it becomes desirable to abort the procedure without deploying the needles and suture material.

In one embodiment, device 200 may include a catheter hemostasis valve proximal of guidewire exchange port 210. The valve may be positioned within catheter 208 and may include one or more flexible valves with an extending body to form a lumen between the valve and guidewire exchange port 210 to facilitate introduction of a guidewire with a ramp to ease the transition to the lumen. A stopper on the valve may help secure the valve within catheter 208, such as by using adhesives, crimping ring, friction or any other suitable methods. The flexible valve(s) may be configured to allow the guidewire to pass through and to block blood flow when the guidewire is withdrawn.

Figure 3:
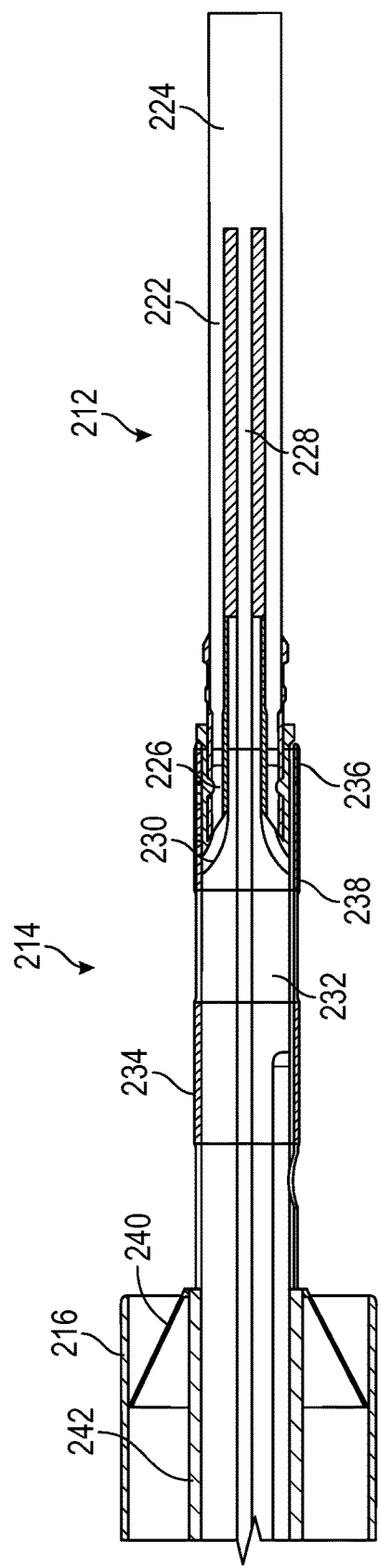
FIG. 3 schematically depicts a detail view of a needle deployment assembly and stabilizer of a suture delivery device, according to one embodiment.

Further details regarding this embodiment are depicted in FIG. 3, which schematically shows needle deployment assembly 212 and stabilizer 214. Needle deployment assembly 212 includes a plurality of needle bases 222 projecting proximally from needle pushing element 224, which may be implemented as a piston or other suitable structure, with each needle having a detachable needle tip 226. Suture material may be threaded through or otherwise secured to an aperture in needle tip 226 (not shown in the figure for the sake of clarity). Trigger wire 228 is secured to piston 224 and extends proximally to handle 202 for actuation by plunger 206 as described in further detail below. For delivery, needle bases 222 and tips 226 are positioned distally of corresponding ramps 230 formed at the distal end of shaft 232. Trigger wire 228 is slidably disposed coaxially within shaft 232 so that relative proximal movement of trigger wire 228 causes needle bases 222 and tips 226 to be deflected radially outward to a piercing angle by ramps 230. Stabilizer 214 is formed by proximal band 234 and distal band 236 that are joined by at least one deflectable wing 238. Proximal band 234 is secured to catcher tube 242, which is coaxially disposed and slidable over shaft 232. In turn, catcher 240 is coaxially disposed and slidable within sheath 216. Correspondingly, distal band 236 is secured to shaft 232. By moving catcher 240 distally relative to shaft 232, the distance between proximal band 234 and distal band 236 may be decreased, causing deflectable wings 238 to project radially outwards to expand stabilizer 214 from its insertion profile.

Figure 4:
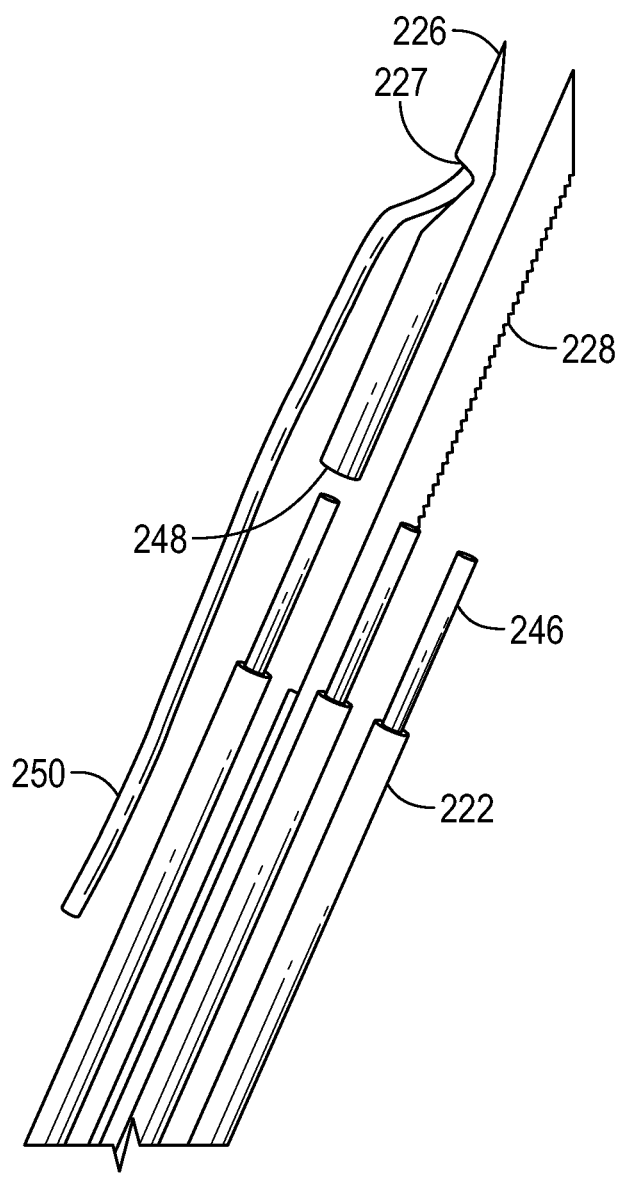
FIG. 4 schematically depicts a needle tips and needle bases, according to one embodiment.
Figure 5:
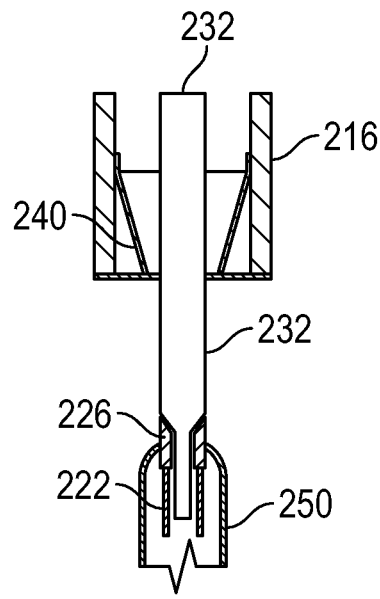
FIG. 5-8 schematically depict engagement of needle tips with a catcher, according to one embodiment.

Details regarding needle assembly 212 are shown in FIG. 4, which schematically depicts the interaction between needle bases 222 and needle tips 226. As shown, each needle base 222 may include post 246 configured to fit within recess 248 of needle tip 226. It may be desirable to position needle tips 226 at a specific rotational orientation with respect to needle bases 222. In one aspect, an asymmetric configuration of post 246 and corresponding recess 248 may secure needle tips 226 at the desired rotational orientation. For example, ribs or other similar features on post 246 may mate with complementary features of recess 248. Other means of securing needle tip 226 to needle base 222 may be employed as desired, such as using a post on the needle tip and a recess in the base. Suture material 250 may be retained in aperture 227 of needle tip 226 using any suitable method, such as crimping, heating, knotting or using adhesives or plug. As noted, needle tips 226 may be detachable from needle bases 222. A variety of techniques may be employed to achieve a desired degree of retention between needle tip 226 and base 222. For example, needle tip 226 may be crimped prior to or after placement on post 246 or some other form of structural interaction may be created. In other embodiments, adhesive may be used or recess 248 may be sized somewhat smaller than post 246 and needle tip 226 may have a split, allowing the elasticity of the tip material to retain it in position. The surface quality and coating of post 246 may also influence the retention of needle tip 226. For example, one or both of needle base 222 and needle tip 226 may be formed from a nickel-titanium alloy such as Nitinol® having super elastic and shape memory characteristics. In one aspect, either or both of needle base 222 and needle tip 226 may have a layer of nitinol oxide to have a proper retention. Although embodiments are discussed in the context of four needles, any suitable number of needles may be employed as desired.

Figure 6:
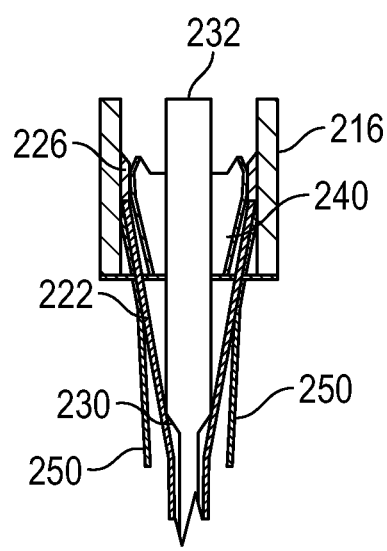
Figure 7:
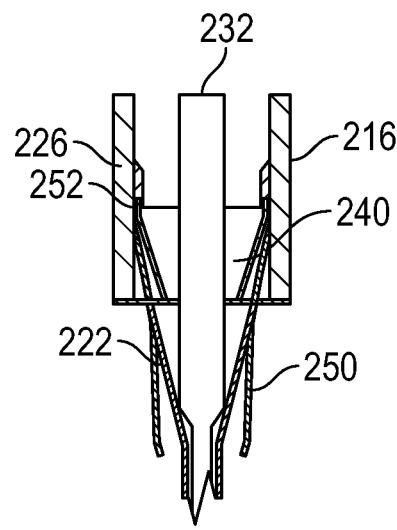
Figure 8:
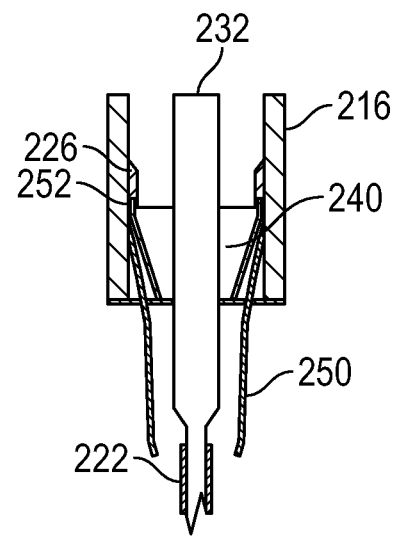

As noted, suture delivery with needle deployment assembly 212 may involve an outward radial deflection of the needles to a piercing angle configured to penetrate the sandwiched tissue from a distal to proximal direction, followed by the capture of at least a portion of the needles, such as needle tips 226 carrying suture material 250. Details regarding aspects of these operations are schematically illustrated in the sequence of FIGS. 5-8. Beginning with FIG. 5, needle tips 226 and needle bases 222 exhibit a reduced profile for insertion by conforming to shaft 232, such as by lying in recesses. Next, FIG. 6 shows that needle tips 226 and needle bases 222 have been driven proximally by needle pushing element 224 and trigger wire 228 as described in reference to FIG. 3. Needle tips 226 and needle bases 222 are deflected outwards by ramps 230 and enter a radial space between sheath 216 and catcher 240. Catcher 240 may employ a conically shaped distal end to help guide the needles into this space. As shown in FIG. 7, once needle tips 226 extend proximally past catcher 240, they may be engaged by a proximal edge 252 of catcher 240 so that they are retained when needle bases 222 are withdrawn distally. Finally, FIG. 8 shows that needle bases 222 have been fully withdrawn distally and once again have a reduced profile by conforming to shaft 232. Needle tips 226, and correspondingly suture material 250, are retained by proximal edge 252 of catcher 240. The conical configuration of catcher 240 may also facilitate travel of needle tip 226 in a proximal direction while resisting travel in the distal direction.

Sheath 216 defines an outer boundary of needle travel path so that catcher 240, coaxially disposed inside the sheath 216, defines the inner boundary. Sheath 216 and catcher 240 may be sized and positioned relative to each other to either define a small radial gap or to be in contact radially at one point or more. Needle tips 226 may pass longitudinally between sheath 216 and catcher 240. In one embodiment, a small gap may exist between catcher 240 and sheath 216 and may be sized to allow needle passage until sufficient friction retain at least a portion of the needle(s) between catcher 240 and sheath 216. Needle capture and retention may be created by friction against catcher 240 and sheath 216 having sufficient force to disengage needle tip 226 from needle base 222 when needle deployment assembly 212 is retracted in the distal direction. Alternatively, proximal edge 252 of catcher 240 may be in contact with sheath 216 so that no gap or a gap smaller than the dimension of needle tip 226 exists, but one or both the materials are sufficiently compliant to deform and allow passage of needle tip 226. In one aspect, needle tip 226 may be wider in dimension than needle base 222 to facilitate engagement with proximal edge 252. For example, the needle tip and needle base may be 0.5 mm and 0.4 mm in outer diameter respectively. In embodiments exhibiting a radial gap between sheath 216 and catcher 240, the space may be substantially constant longitudinally along the device or may taper, so that it is wider near the distal end to facilitate entry of needle tip 226 and narrower towards the proximal end to provide increasing friction for retention of needle tip 226. The friction may be enhanced by selecting materials having the desired properties for catcher 240 and/or sheath 216. Similarly, the friction may also be increased by the mechanical design. In other embodiments, significant friction between needle tip 226 and needle base 222 may not be required. Needle disengagement may also be facilitated by providing a curved pathway between catcher 240 and sheath 216 though which the needles pass when moved relatively proximally.

Figure 9:
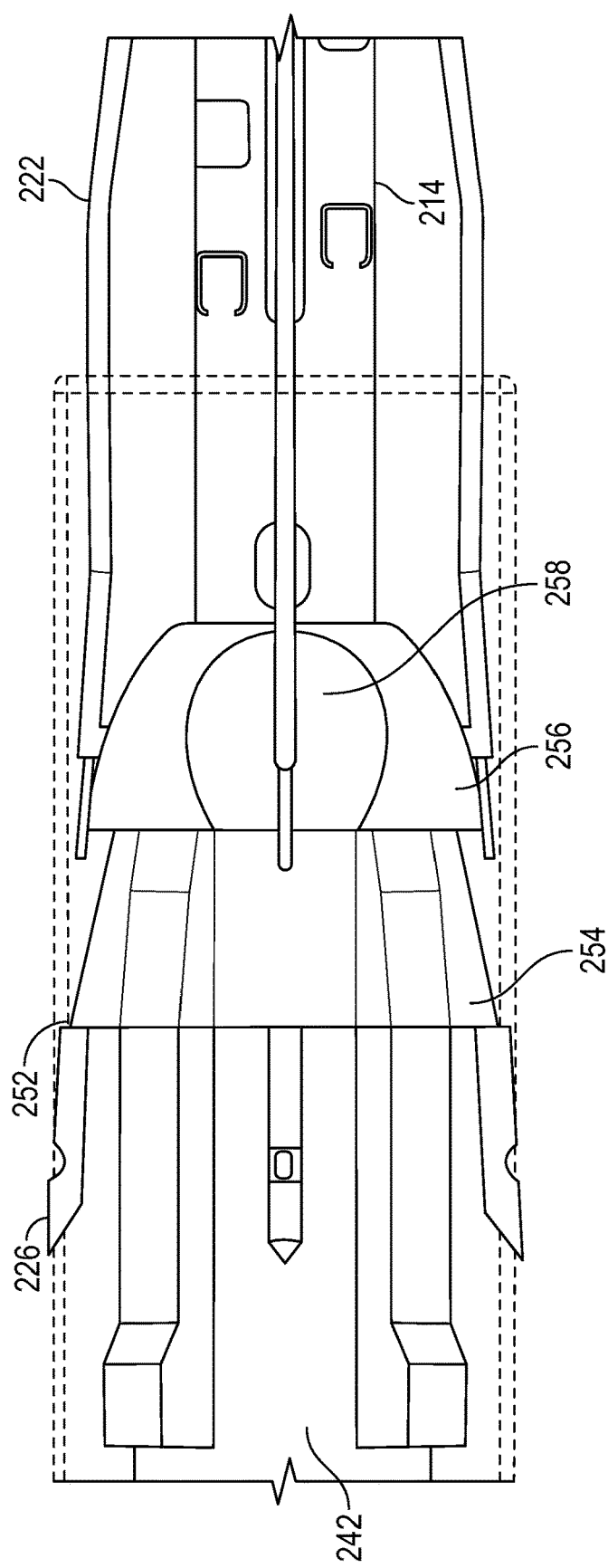
FIG. 9 schematically depicts engagement of needle tips with a catcher dish, according to one embodiment.

Turning now to FIG. 9, in an embodiment, catcher 240 may include a dedicated element for engaging needle tips 226 for retention, such as catcher dish 254 positioned proximally of stabilizer interface 256. Both catcher dish 254 and stabilizer interface 256 may be carried by catcher tube 242. The material of stabilizer interface 256 may be selected to form a rigid connection with stabilizer 214 while the material of catcher dish 254 may be selected to exhibit the resilience or friction properties described above to allow needle tip 226 to pass in the proximal direction but resist withdrawal in the distal direction. In one aspect, catcher dish 254 may be formed from titanium alloys, such as Ti6Al4V, stainless steel, or other similar materials. In one aspect, catcher dish 254 may be configured to allow needle tips 226 to penetrate the material such that sufficient engagement is created to retain needle tips 226 when needle bases 222 are withdrawn. Similarly, catcher dish 254 may have slits through which needle tips 226 pass when moved to the proximal position. The proximal deflection of the material around the slits when needle tips 226 pass from the distal side to the proximal side may create an interface to facilitate retention of needle tips 226.

Stabilizer interface 256 may include guides 258 or similar structural features to help guide needle tips 226 as they travel in the proximal direction. In one aspect, catcher dish 254 may exert a light, outward force on sheath 216. The conical shape of catcher dish 254 may act to guide needle tip 226 through the space between sheath 216 and catcher 240. Where catcher dish 254 contacts sheath 216, the material may slightly deform inward to allow needle tip 226 penetration. When needle tip 226 has completely passed proximal edge 252, catcher dish 254 may rebound towards sheath 216 to functions as mechanical stop against movement in the distal direction. Accordingly, when needle deployment assembly 212 is retracted, needle tip 226 may be detached from needle base 222. Any gap between catcher dish 254 and sheath 216 will substantially close once needle base 222 is retracted. Needle tip 226 carrying suture material 250 (not shown here for clarity) may then be retained proximal to catcher dish 254.

Figure 10:
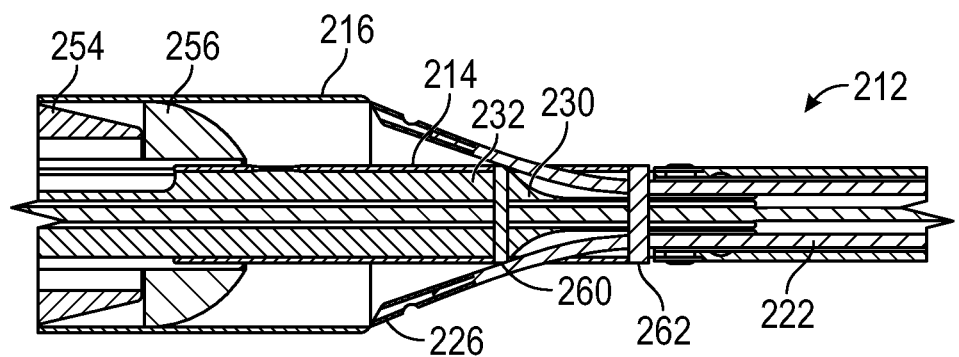
FIG. 10 schematically depicts deflection of needles to a piercing angle, according to one embodiment.

Turning now to FIG. 10, additional details regarding an embodiment of needle deployment assembly 212 are depicted. As shown, needle bases 222 and needle tips 226 have been moved proximally and deflected radially outwards. In this drawing, stabilizer 214 is shown in its unexpanded configuration so as not to obscure aspects related to needle deployment, however, as described below, during normal operation stabilizer 214 may be expanded for needle deployment. Ramps 230 guide needle tips 226 and needle bases 222 over proximal ring 260. In some embodiments, proximal ring 260 may be omitted and ramps 230 alone used to deflect the needles to the desired piercing angle. Further, needle tips 226 and needle bases 222 travel through and are constrained by distal ring 262 so that they conform to shaft 232 distally of distal ring 262. Distal ring 262 may serve as a guide for the plurality of needles to prevent dislodging or buckling. When the needles are deployed, the needle tips 226 and needle bases 222 extend underneath distal ring 262 and travel over proximal ring 260 causing the needles to protrude out at a piercing angle. The piercing angle may be established by the distance between proximal ring 260 and distal ring 262 and/or by their relative diameters, as well as by the angle of ramp 230.

Figure 11:
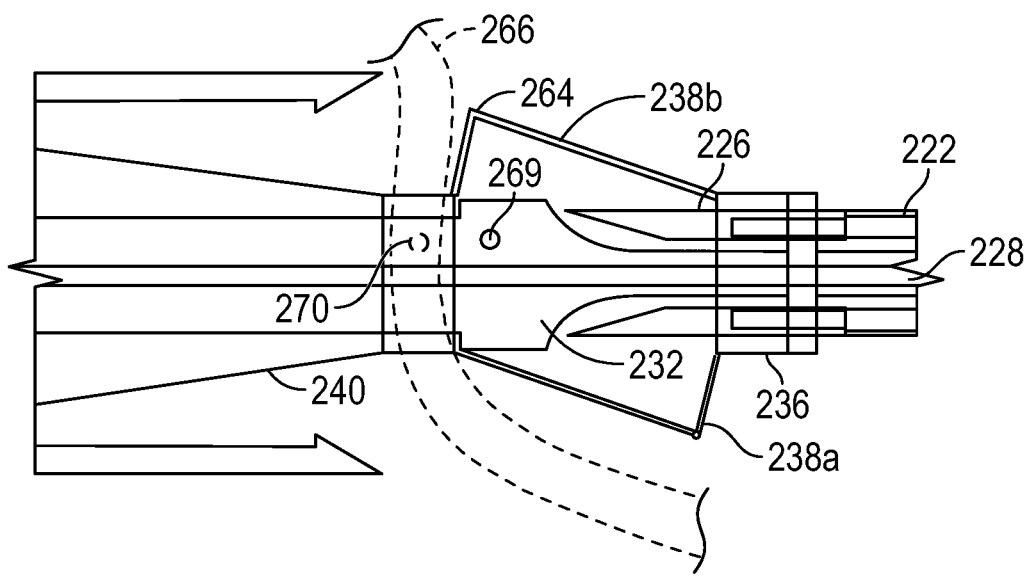
FIG. 11 schematically depicts the sandwiching of tissue to be sutured between an expanded stabilizer and a sheath, according to one embodiment.

Further details regarding one embodiment of stabilizer 214 are schematically depicted in FIG. 11. In comparison with FIG. 3, catcher tube 242 has been moved distally with respect to shaft 232. As described above, proximal band 234 of stabilizer 214 is secured to catcher tube 242 while distal band 236 is secured to shaft 232. The relative decrease in distance between proximal band 234 and distal band 236 has caused the deflectable wings 238 to project radially outwards, expanding stabilizer 214. Thus, relative movement between sheath 216 and shaft 232 may sandwich tissue 266 to be sutured between expanded stabilizer 214 and sheath 216. Deflectable wings 238 may feature hinge points 264 at desired locations, including locations intermediate along the deflectable wing and/or at connections to proximal band 234 and distal band 236, to help control the expanded profile of stabilizer 214. For example, device 200 may be inserted at an angle of approximately 45° with respect to the vessel wall having the puncture to be closed. Correspondingly, the relative plane of tissue 266 may not be substantially perpendicular to the longitudinal axis of device 200. By selecting appropriate hinge points 264, deflectable wings 238 may be configured to provide a profile that more closely tracks the anticipated angle of tissue 266. In the embodiment shown, fore deflectable wing 238a may expand to present a relatively shallower angle with respect to the longitudinal axis of device 200. Similarly, aft deflectable wing 238b may present a relatively sharper angle when expanded. As shown, the angles presented by deflectable wings 238a and 238b may provide enhanced support to stabilize tissue 266. In one aspect, tissue adjacent the more acute angle of insertion of device may exhibit a greater tendency to flow downwards and become inverted. The sharper angle presented by deflectable wing 238b may help lift the inverted tissue. In some embodiments, a single deflectable wing corresponding to deflectable wing 238b may be sufficient to stabilize the sandwiched tissue.

Further, FIG. 11 also shows that a shaft 232 may have distal bleed back ports 269 and 270 adjacent stabilizer 214, which are in communication with bleed back indicator 218 on handle 202. When device 200 is positioned at a desired location within the patient's vasculature, blood may enter ports 269 and/or 270, travel through a channel in shaft 232 and be visible at indicator 218. As such, blood flow at indicator 218 may be provide feedback regarding the relative position of device 200 with respect to the patient's vessel. In one aspect, either or both ports 269 and 270 may be employed. Port 269 will continue to provide bleeding indication after expansion of stabilizer 214 and the sandwiching of tissue 266 against sheath 216. In comparison, port 270 may provide bleeding indication when first positioned in the vessel, but may be blocked by tissue 266 when the sandwich is created between stabilizer 214 and sheath 216, thus signaling that the sandwich has been created.

Additional exemplary embodiments showing different suitable configurations of stabilizer 214 are depicted in FIGS. 12-19. Generally, FIGS. 12, 14, 16 and 18 show plan views of alternative configurations of stabilizer 214 represented as two-dimensional (2-D) views of a stabilizer that has been cut along the longitudinal axis and laid out flat, such that the joining the opposing side edges forms a cylinder. The characteristics of each deflectable wing 238 may be established by the relative positioning of proximal, distal and intermediate hinge points 264. The overall length of each deflectable wing 238 depends upon the relative distance between the proximal and distal hinge points 264, while the positioning of the intermediate hinge point 264 establishes lengths of proximal and distal portions of each deflectable wing 238 and controls the angle formed by the proximal portion of the deflectable wing 238 with respect to the longitudinal axis of device 200. In turn, FIGS. 13, 15, 17 and 19 show the expanded configurations when positioned within the patient's vasculature with an insertion angle of approximately 45° and the relative angles formed by the deflectable wings in relation to the vessel wall of the patient. In these views, the side deflectable wings are not shown for the sake of clarity. Although embodiments are discussed in the context of four deflectable wings 238, other configurations employing any suitable number of wings may be employed as desired.

Figure 12:
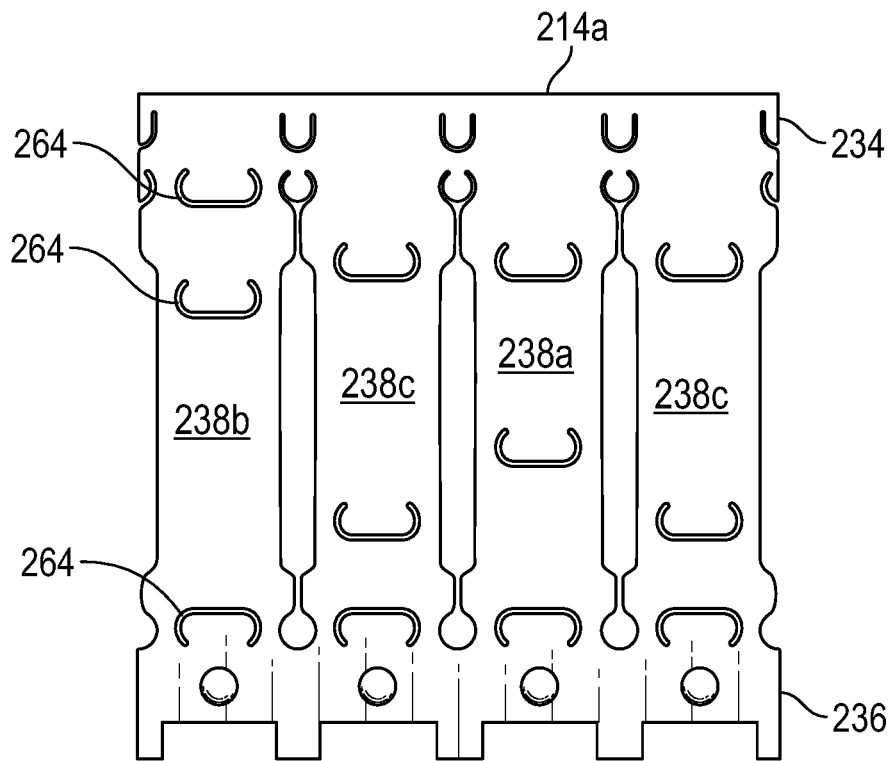
FIG. 12 schematically depicts a first embodiment of a stabilizer, according to the disclosure.
Figure 13:
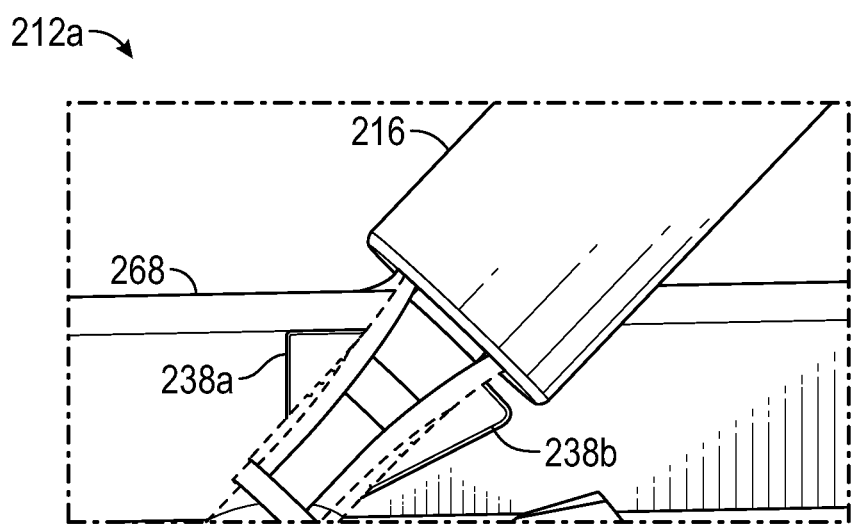
FIG. 13 schematically depicts the stabilizer embodiment of FIG. 12 in relation to a patient's vessel wall.

With regard to FIGS. 12 and 13, a first exemplary configuration is shown for stabilizer 214a. In this embodiment as depicted in FIG. 12, fore deflectable wing 238a has substantially equal proximal and distal portions. Aft deflectable wing 238b has a longer overall length and a relatively shorter proximal portion to establish a relatively sharp angle with respect to the longitudinal axis. Side deflectable wings 238c have equivalent overall lengths as fore deflectable wing 238a and relatively longer proximal portions. As shown in the corresponding FIG. 13, the proximal portion of fore deflectable wing 238a exhibits an angle substantially similar to vessel wall 268 while the proximal portion of aft deflectable wing 238b forms a sharper angle. Aft deflectable wing 238b is also positioned relatively more proximal as established by the proximal hinge point 264.

Figure 14:
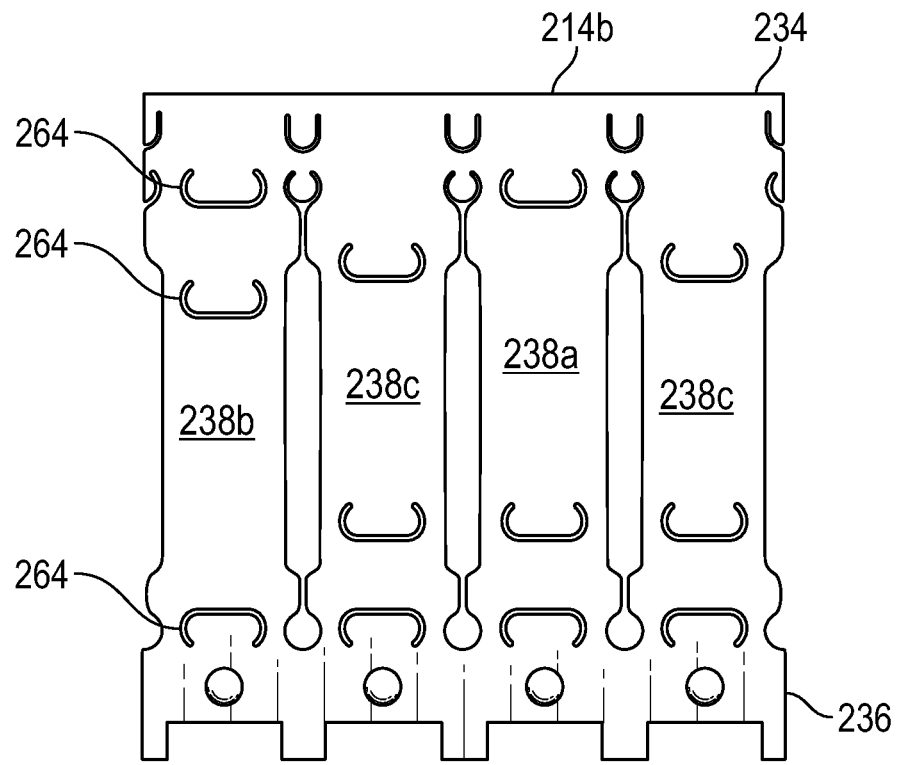
FIG. 14 schematically depicts a second embodiment of a stabilizer, according to the disclosure.
Figure 15:
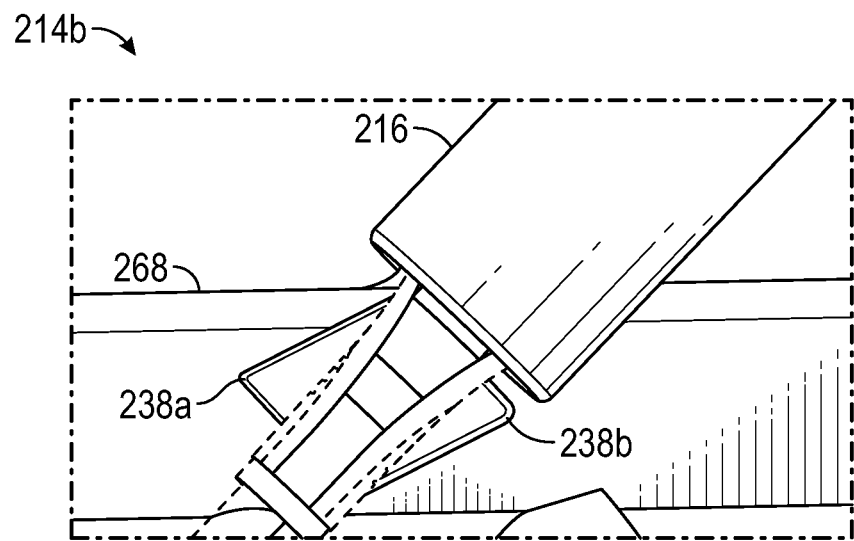
FIG. 15 schematically depicts the stabilizer embodiment of FIG. 14 in relation to a patient's vessel wall.

Next, FIGS. 14 and 15 illustrate a second exemplary configuration in the context of stabilizer 214b. Here, FIG. 14 depicts fore deflectable wing 238a and aft deflectable wing 238b as having substantially equal lengths, with the proximal portion of fore deflectable wing 238a similar in length to the distal portion of aft deflectable wing 238b to generate opposing symmetry. As shown in the corresponding FIG. 15, the proximal portion of fore deflectable wing 238a exhibits a relatively shallow angle with the longitudinal axis and a relatively perpendicular relationship to the proximal portion of aft deflectable wing 238b.

Figure 16:
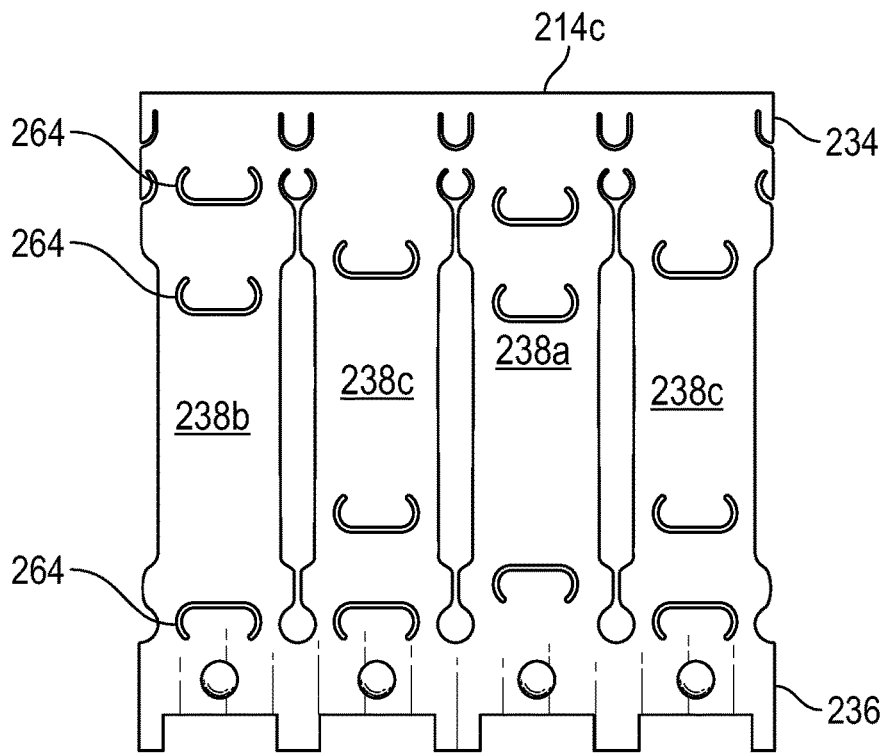
FIG. 16 schematically depicts a third embodiment of a stabilizer, according to the disclosure.
Figure 17:
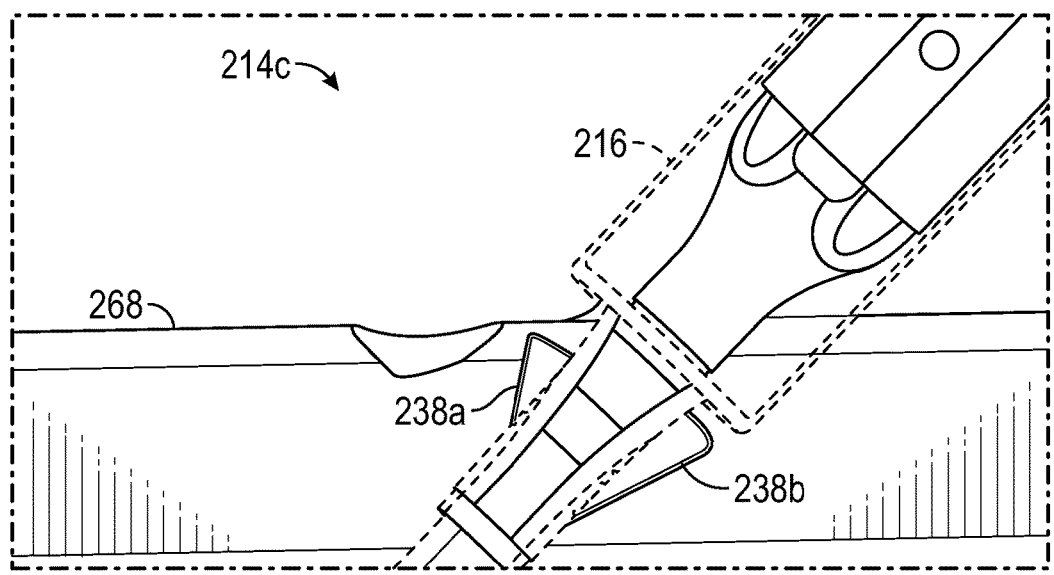
FIG. 17 schematically depicts the stabilizer embodiment of FIG. 16 in relation to a patient's vessel wall.

The third exemplary embodiment shown in FIGS. 16 and 17 includes stabilizer 214c. As depicted in FIG. 16, fore deflectable wing 238a and aft deflectable wing 238b have similar overall lengths and similar proportions of proximal and distal portions. Side deflectable wings 238c have relatively shorter overall lengths with relatively longer proximal portions. Accordingly, FIG. 17 shows that both the proximal portion of fore deflectable wing 238a and the proximal portion of aft deflectable wing 238b exhibit a relatively sharp angle with respect to the longitudinal axis.

Figure 18:
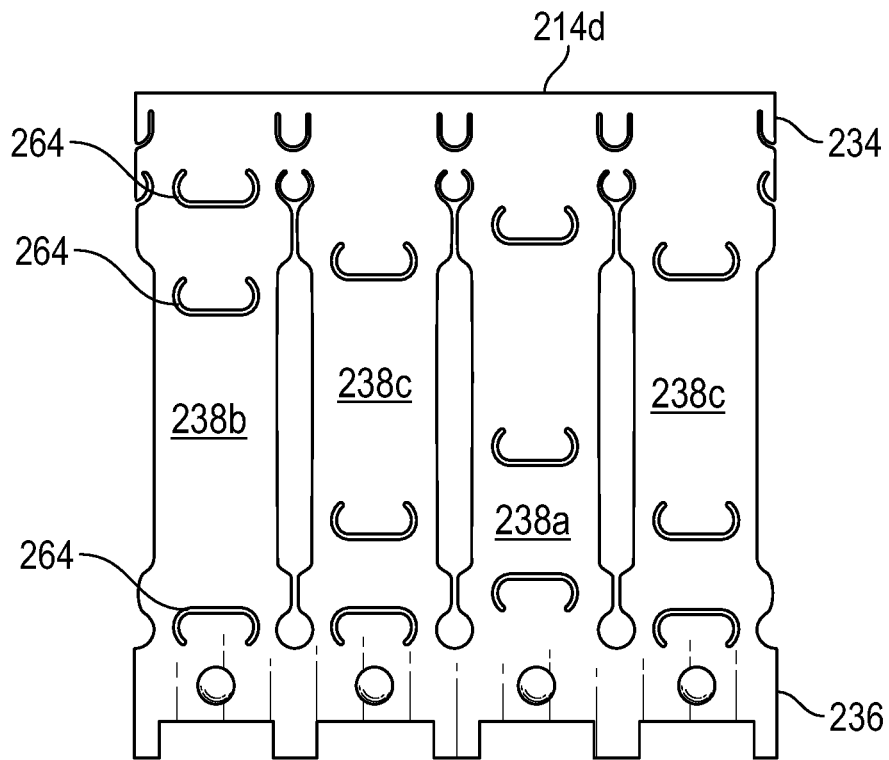
FIG. 18 schematically depicts a fourth embodiment of a stabilizer, according to the disclosure.
Figure 19:
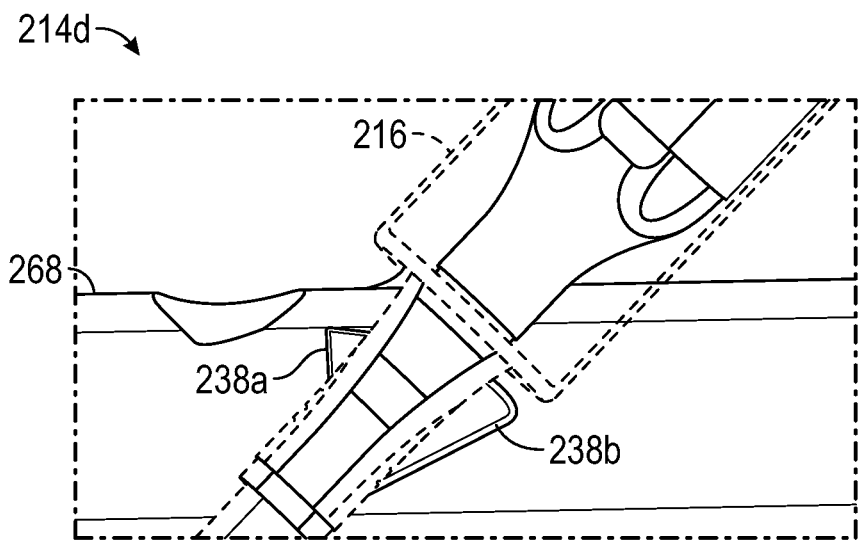
FIG. 19 schematically depicts the stabilizer embodiment of FIG. 18 in relation to a patient's vessel wall.

With regard to FIGS. 18 and 19, a fourth exemplary configuration is shown for stabilizer 214d. As depicted in FIG. 18, fore deflectable wing 238a has substantially equal proximal and distal portions. Aft deflectable wing 238b has a longer overall length and a relatively shorter proximal portion to establish a relatively sharp angle with respect to the longitudinal axis. In comparison with stabilizer 214a, fore deflectable wing 238b is positioned relatively more proximal. Side deflectable wings 238c have equivalent overall lengths as fore deflectable wing 238a and relatively longer proximal portions. As shown in the corresponding FIG. 19, the proximal portion of fore deflectable wing 238a exhibits an angle substantially similar to vessel wall 268 while the proximal portion of aft deflectable wing 238b forms a sharper angle.

From the above, it will be appreciated that employing stabilizer designs having asymmetrical deflectable wings provide a number of benefits. By adjusting length, position and hinge points, stabilizer 214 may be configured to conform more closely to the anatomy of the targeted vessel wall adjacent the puncture being closed. Interaction between the deflectable wings, and in particular, the aft deflectable wing 238b, and sheath 216 may help lift inverted tissue. By providing positive interaction with tissue 266 through both stabilizer 214 and sheath 216 may operate to anchor device 200 to vessel wall 268 and provide tactile feedback about correct positioning. Further, by maintaining a distance to needle tips 226 prior to penetration, deflectable wings 238 may allow needle tips 226 and needle bases 222 to be deployed into a correct piercing angle before intersecting the sandwiched tissue. The configuration of stabilizer 214 may also be selected to minimize sharp edges and openings to improve smoothness and reduce damage to the vessel wall. Similarly, side deflectable wings 238c may be configured to minimize impact with the vessel but provide structural integrity to the expanded stabilizer.

As described above, the operations of stabilizer 214 and sheath 216 to sandwich tissue followed by the delivery of suture material 250 via needle tips 226 by movement of needle deployment assembly 214 and capture of the needle tips 226 with catcher 240 may involve the relative movement between coaxial elements of this disclosure, such as trigger wire 228, shaft 232, catcher tube 242 and/or sheath 216. For example, stabilizer 214 may be expanded by moving catcher tube 242 distally relative to shaft 232 to compress proximal band 234 and distal band 236 together. In another aspect, tissue 266 may be sandwiched by moving sheath 216 and expanded stabilizer 214 together, such as through distal movement of sheath 216 relative to shaft 232. In yet another aspect, needle tips 226 and needle bases 222 may be deflected into a piercing angle and driven proximally through sandwiched tissue 266 by the relative proximal movement of trigger wire 228 with respect to shaft 232. Following capture of needle tips 226, needle bases 222 may be returned to their insertion profile by the relative distal movement of trigger wire 228 with respect to shaft 232. Additionally, stabilizer 214 may be returned to its unexpanded insertion profile by the relative proximal movement of catcher tube 242 with respect to shaft 232.

Accordingly, aspects of this disclosure include the use of handle 202 to effect the desired relative movements of the noted coaxial elements in order to perform the associated operations. Notably, embodiments include the use of handle 202 to coordinate multiple movements of the coaxial elements to perform one or more of the operations discussed above with respect to FIG. 1, including by actuating slider 204 and/or plunger 206. To help illustrate these techniques, FIGS. 20-27 schematically show details of handle 202 and associated components linked to slider 204 and plunger 206 and their relative movements when actuated.

Figure 20:
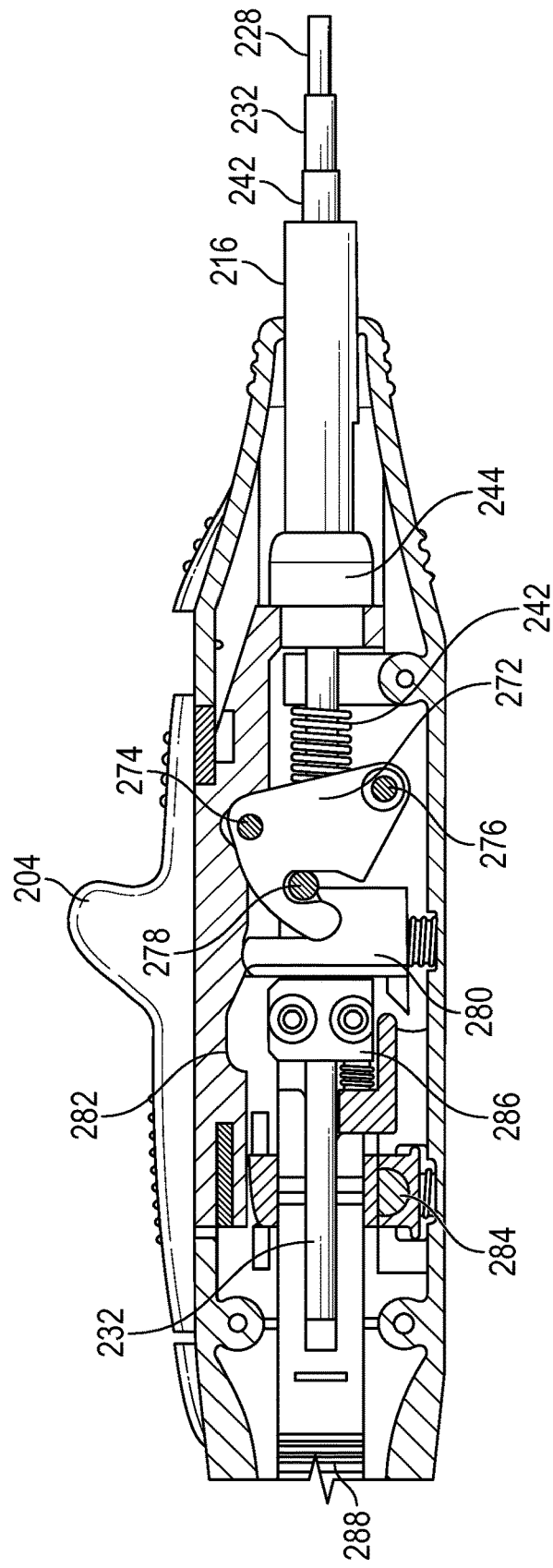
FIG. 20 schematically depicts a proximal position of a first actuator, according to one embodiment.

Starting with FIG. 20, a side view of handle 202 is shown with slider 204 in its most proximal position which corresponds to stabilizer being in its unexpanded configuration for delivery. Slider 204 is directly coupled to sheath 216, such that distal motion of slider 204 is translated to distal motion of sheath 216. Slider 204 is also linked to stabilizer follower 272 by pin 278, such that distal motion of slider 204 pivots stabilizer follower 272 on axle 276. Pin 278 is secured to catcher tube 242 and is captured by a slot in stabilizer follower 272, so that catcher tube 242 is also moved distally by slider 204. Stabilizer control 280 is biased upwards towards slider 204, having a position dictated by slider profile 282. Trigger safe 284 is also biased upwards and constrained by slider profile 282. Shaft 232 extends coaxially within sheath 216 and catcher tube 242 and is secured by base 286 to handle 202. Trigger wire 228 is coupled to trigger rack 288, such that proximal motion of trigger rack 288 withdraws trigger wire 228 coaxially within shaft 232.

In this configuration, trigger safe 284 locks trigger rack 288 in position to prevent movement of trigger wire 228 until the tissue has been sandwiched.

Figure 21:
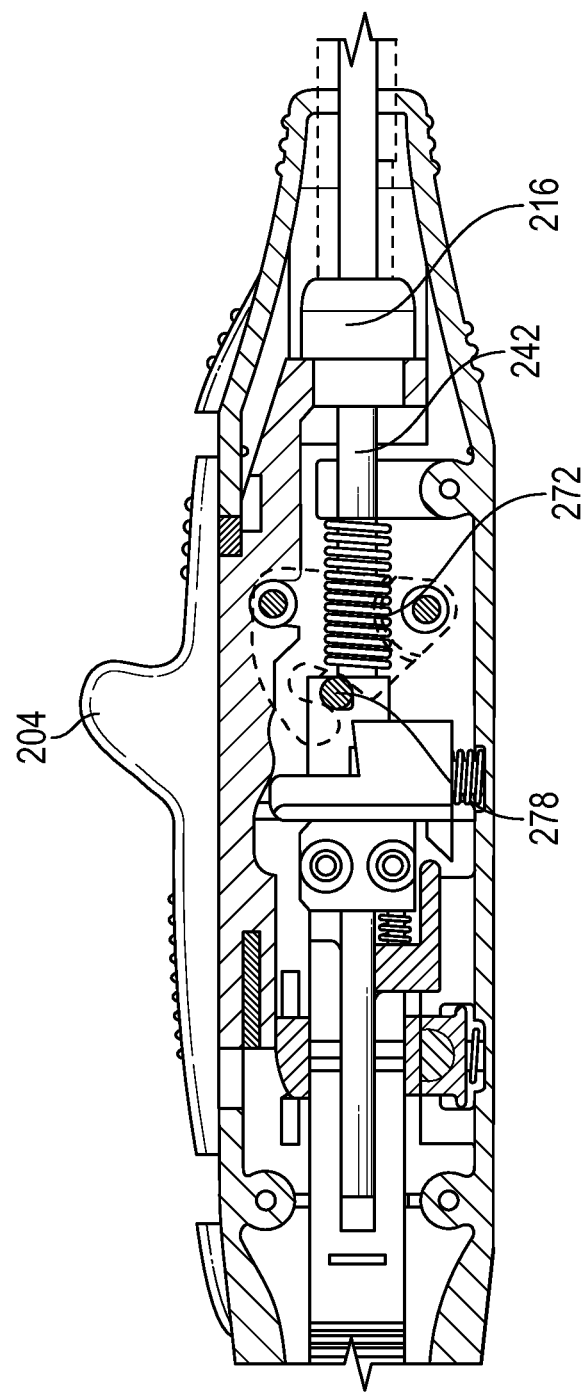
FIG. 21 schematically depicts an intermediate position of a first actuator, according to one embodiment.
Figure 22:
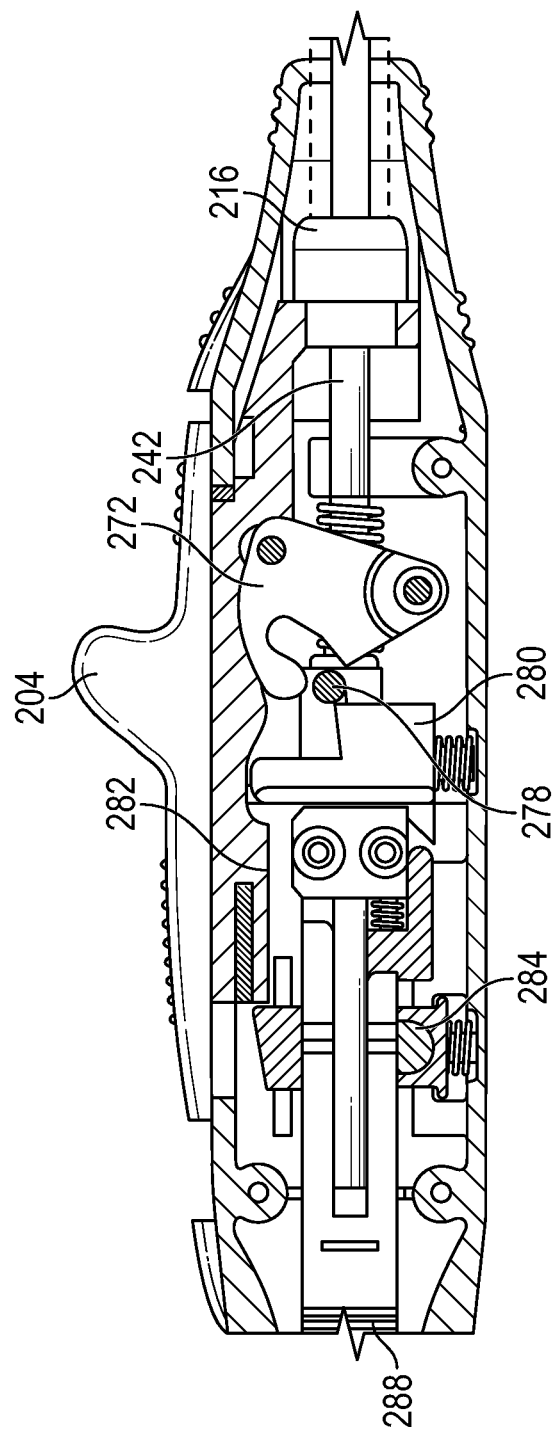
FIG. 22 schematically depicts a distal position of a first actuator, according to one embodiment.

Once device 200 has been positioned at a desired location within the patient's vasculature, such as through use of bleed back indicator 218 as discussed above, the operator may expand stabilizer 214 and sandwich tissue between the expanded stabilizer and sheath 216 by actuating slider 204. As shown in FIG. 21, as slider 204 is moved distally, sheath 216 is also moved distally relative to handle 202. Simultaneously, the distal motion of slider 204 is translated through stabilizer follower 272 to move catcher tube 242 distally relative to handle 202, and correspondingly, relative to shaft 232. At the position indicated by this figure, catcher tube 242 is near the end of its range of motion, such that stabilizer 214 has been expanded and further distal movement of stabilizer follower 272 will release pin 278, decoupling catcher tube 242 from slider 204. Continued distal motion of slider 204 results in the configuration shown in FIG. 22. Sheath 216 has been moved distally along with the continued actuation of slider 204 to sandwich tissue between its distal end and expanded stabilizer 214. When slider 204 reaches the most distal position, slider profile 282 allows stabilizer control 280 to travel upwards and engage pin 278 to prevent proximal movement of catcher tube 242. Similarly, slider profile 282 also releases trigger safe 284, allowing it to travel upwards and unlock trigger rack 288. In this upward position, trigger safe 284 also engages the proximal end of slider profile 282 to lock slider 204 in the distal position. At this stage, full actuation of slider 204 has expanded stabilizer 214 and sandwiched tissue between stabilizer 214 and the distal end of sheath 216. In some situations, it may be desirable to discontinue the operation before deploying the needles and suture material. For example, the operator may encounter calcified tissue or some other condition that contraindicate suture delivery. Release trigger 220, shown in FIG. 2, may be coupled to trigger safe 284 to allow the operator to manually return trigger safe 284 to its downward position that relocks trigger rack 288 and unlocks slider 204, so that the operator may move slider 204 proximally and reverse the operations described above, releasing the sandwiched tissue and causing stabilizer 214 to assume its unexpanded configuration.

Figure 23:
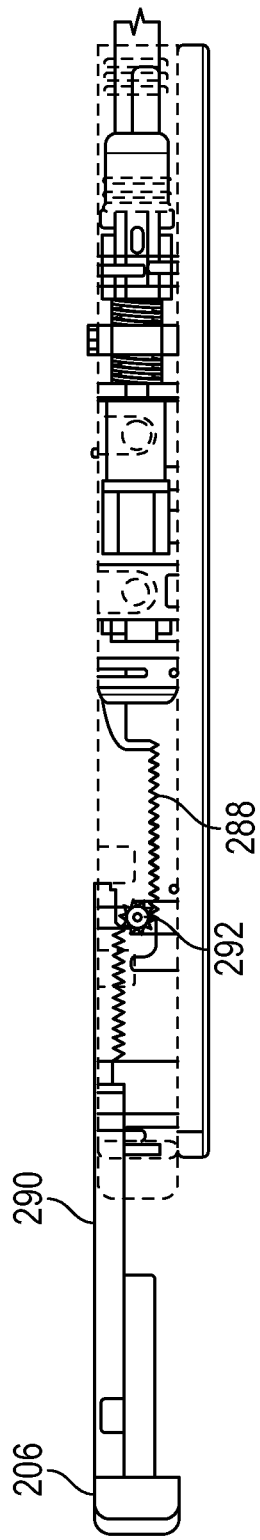
FIG. 23 schematically depicts a proximal position of a second actuator, according to one embodiment.

After sandwiching the tissue between stabilizer 214 and sheath 216 by actuation of slider 204, plunger 206 may be actuated to deploy needle tips 226 and needle bases 222 so that they penetrate the sandwiched tissue and are captured by catcher 240 and sheath 216. FIG. 23 schematically depicts a top view of handle 202 with plunger 206 in its most proximal position. Plunger 206 is directly coupled to plunger rack 290 and pinion 292 engages plunger rack 290 and trigger rack 288 for a first range of travel from the most proximal position of plunger 206 to an intermediate position. As described above, slider 204 has been advanced to its most distal position and trigger safe 284 is allowed to travel upwards by slider profile 282, unlocking trigger rack 288. Correspondingly, actuation of plunger 206 distally through the first range of travel rotates pinion 292 to withdraw trigger rack 288 in a proximal direction. Since trigger rack 288 is coupled to trigger wire 228, actuation of plunger 206 through the first range of travel also moves needle pushing element 224 proximally, causing needle bases 222 and needle tips 226 to first deflect outward from the insertion profile shown in FIG. 5 to a piercing angle to penetrate the sandwiched tissue before needle tips 226 travel between catcher 240 and sheath 216 for capture as shown in FIG. 7.

Figure 24:
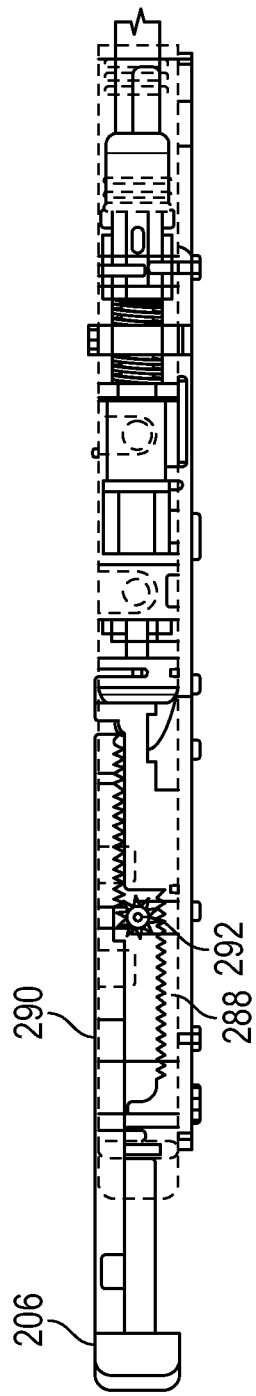
FIG. 24 schematically depicts an intermediate position of a second actuator with the pinion disengaged from the plunger rack, according to one embodiment.
Figure 25:
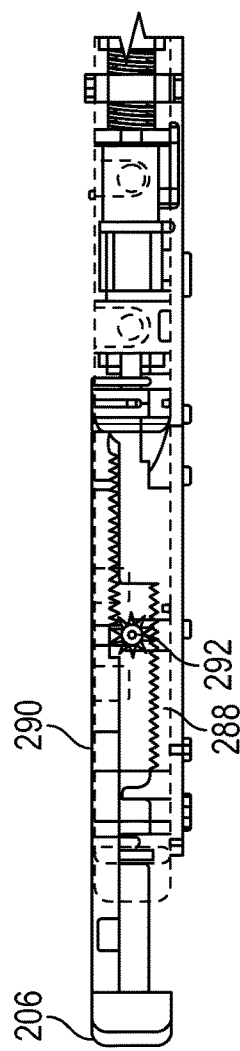
FIG. 25 schematically depicts an intermediate position of a second actuator with the plunger rack engaged with the trigger rack, according to one embodiment.

At the end of the first range of travel of plunger 206, pinion 292 disengages from plunger rack 290 as shown in FIG. 24. At the same point, the distal end of plunger rack 290 directly engages the proximal end of trigger rack 288 so that continued distal motion of plunger 206 through a second range of travel now pushes trigger rack 288 and correspondingly, trigger wire 228, distally to return needle pushing element 224 to its original position. In turn, this motion withdraws needle bases 222 to their insertion profile in which they conform to shaft 232. The most proximal position of plunger 206 of second range of travel is shown in FIG. 25. As can be seen, actuation of plunger 206 through the second range of travel has reversed the direction of trigger rack 288, moving it relatively distal of the position shown in FIG. 24 an amount sufficient to return needle deployment assembly 212 to its original position.

Figure 26:
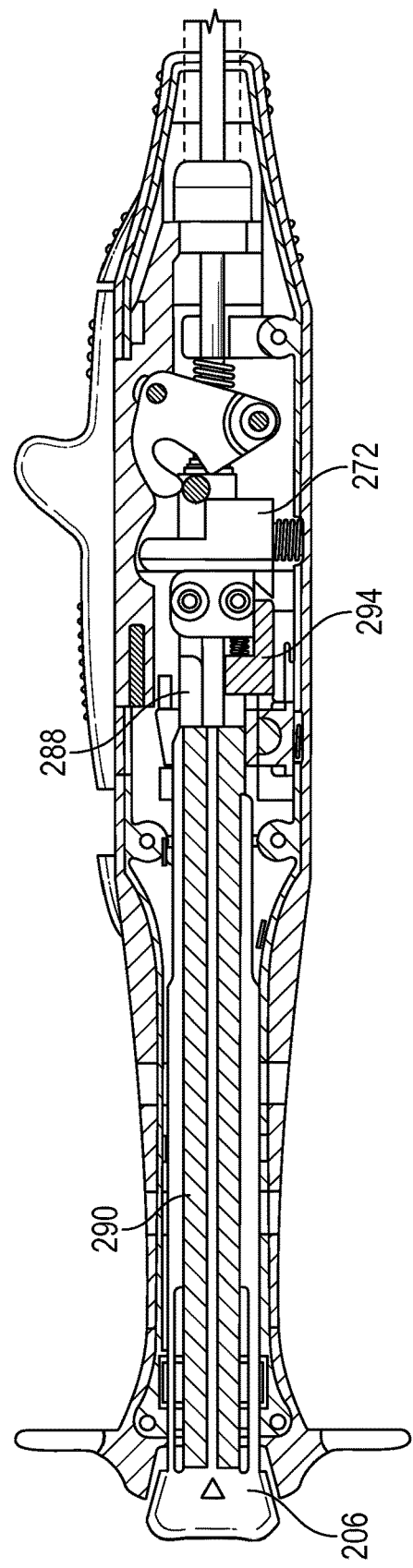
FIG. 26 schematically depicts another view of a second actuator, according to one embodiment.
Figure 27:
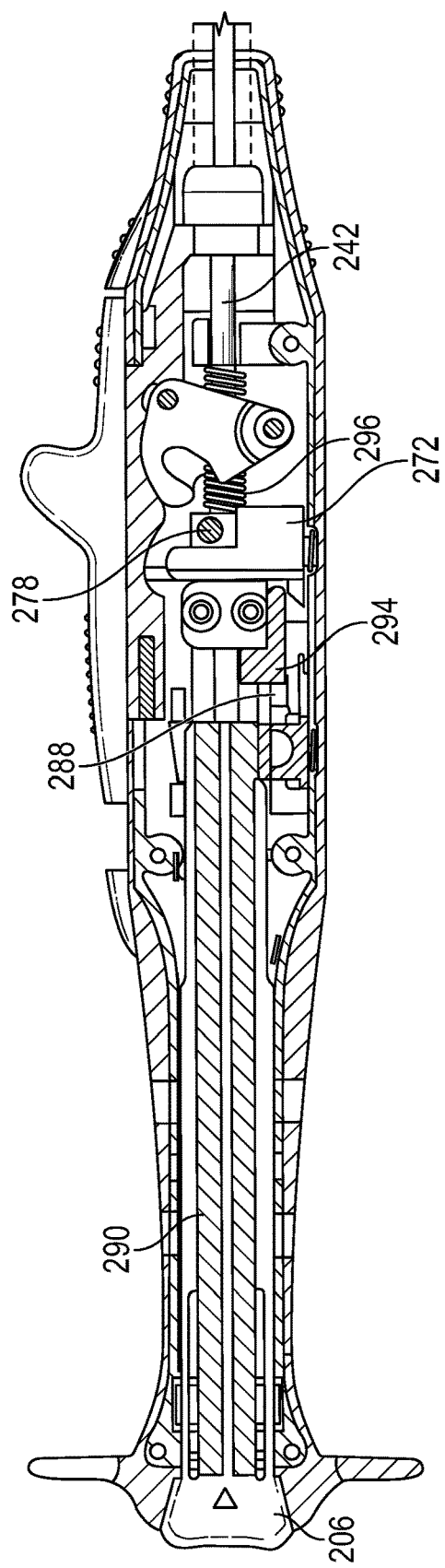
FIG. 27 schematically depicts another view of a second actuator at an end of the second range of travel to disengage the stabilizer control and allow further relative movement between the catcher tube and the shaft so that the stabilizer can return to the unexpanded insertion profile, according to one embodiment.

The configuration of handle 202 resulting from actuation of plunger 206 to a position just prior to its full distal position is shown schematically in the side view of FIG. 26. Engagement between plunger rack 290 and trigger rack 288 has moved trigger rack distally so that the distal end engages reset link 294 which is biased in the proximal direction. The full distal configuration of handle 202 is shown in FIG. 27. The additional distal movement of trigger rack 288 has urged reset link 294 distally, engaging and moving stabilizer controller 272 to its downward position. In turn this frees pin 278, allowing catcher tube 242 to move proximally to its starting position. Catcher tube 242 may be biased in the proximal direction by spring 296. Further, the material of stabilizer 214 may have an elastic property having a tendency for it to return to its unexpanded configuration. For example, stabilizer may be formed from a nickel-titanium alloy such as Nitinol® having super elastic and shape memory characteristics. Accordingly, movement of stabilizer controller 272 to its downward position allows catcher tube 242 to move proximally and stabilizer 214 to assume its insertion profile.

Figure 28:
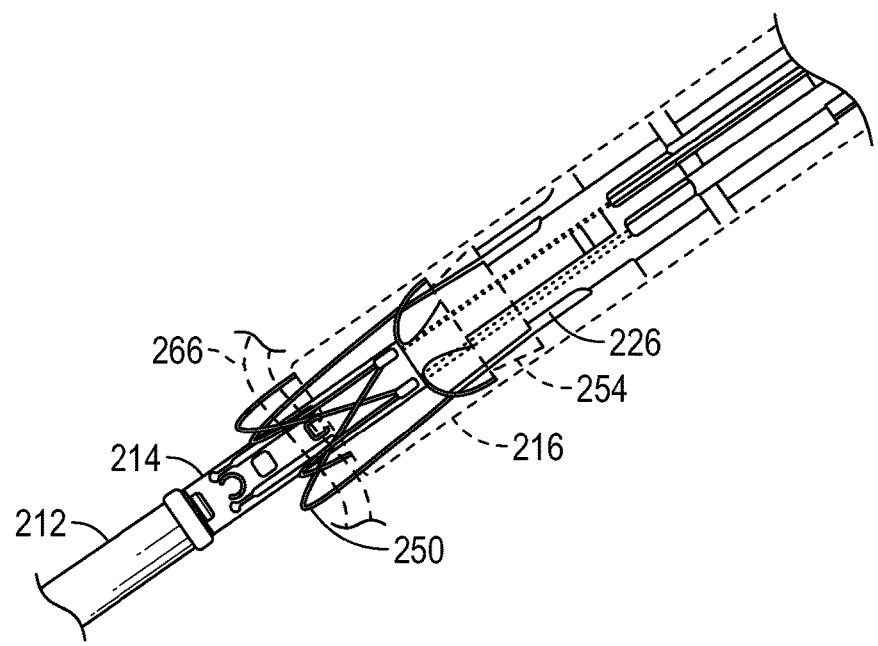
FIG. 28 schematically depicts retention of needle tips by a catcher with suture material passed through sandwiched tissue, according to one embodiment.
Figure 29:
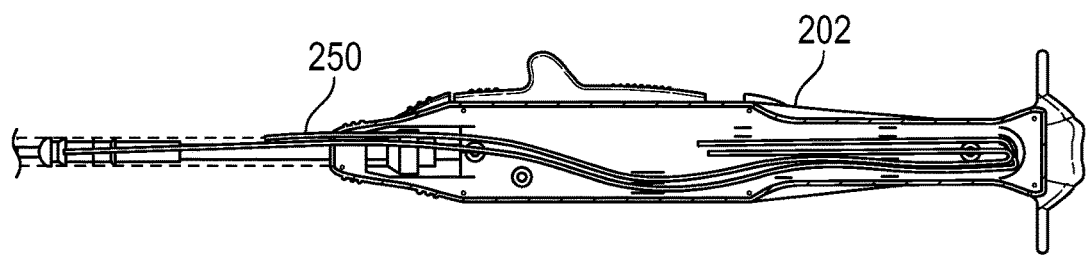
FIG. 29 schematically depicts storage of suture material within a handle of the device, according to one embodiment.

Following actuation of slider 204 and plunger 206 as described above, stabilizer 214 may be returned to its unexpanded configuration and needle deployment assembly 212 may assume it insertion profile as shown in FIG. 28. Further, needle tips 226 have been captured by catcher dish 254 and sheath 216, leaving loops of suture material 250 threaded through tissue 266. At this stage, device 200 may be withdrawn. Excess suture material 250 may be stored in handle 202 as shown in FIG. 29, allowing device 200 to be withdrawn and suture material 250 to spool out, reducing tension to minimize tearing of tissue 266.

As described above, the devices of this disclosure may be used to close and facilitate repair of openings created during intravascular procedures. For example, the Seldinger technique is a known procedure for accessing the femoral artery and suture delivery device 100 may be used to close the opening created in the artery. More generally, the devices of this disclosure may be used for delivery of sutures for closing various sizes of vascular access site, and reducing the time to hemostasis and time to ambulation of patients who have undergone catheterization procedures using sheaths in the range of 5 F-24 F. Still more generally, this disclosure is applicable to any clinical procedure involving closure of incisions or orifices of soft tissues and organs. For example, suture delivery device 200 or an embodiment suitably adapted may be used for closure of soft tissue opening or tear in surgical or interventional procedures such as gastrointestinal perforation, perforated ulcer, closure of trocar incision associated with minimally invasive or natural orifice transluminal endoscopic surgery, closure of patent foramen ovale (PFO), spinal annular repair, and other procedures that may benefit from suturing.

Although the first actuator is described above in the context of slider 204, it will be appreciated that any suitable mechanical means such as a button, a lever, a slider, a trigger, a plunger, a rotator, a crank or other feasible actuator that the operator can use to activate the associated device mechanism of pressing distal device component(s) inside blood vessel and proximal device component(s) outside of blood vessel against vessel wall, thereby sandwich the vessel wall in between the device components. Similarly, although the second actuator is described in the context of plunger 206, any suitable mechanical means such as a button, a lever, a slider, a trigger, a plunger, a rotator, a crank or other feasible actuator that allow the user to activate the associated device mechanism of moving needle(s) carrying suture to penetrate from one side of vessel wall to the other side (e.g., inside vessel wall to outside vessel wall) until needle(s) with suture are captured or retained by proximal device components positioned outside vessel wall. In some embodiments, needle(s) may have parts that can be detached from each other. The needle capture may involve disengaging or detaching needle tip from the needle body or base whereby the needle tip with suture is retained by the proximal device components outside vessel. As noted, the second actuator may have first and second ranges of travel corresponding to relative proximal and distal motion of the needles. Accordingly, a rotational link may provide the desired ranges of travel such as through a first 180° and a second 180°.

A device may have a needle deployment assembly comprising a needle pushing element, such as needle pushing element 224 carrying needle(s) attached to suture material 250 and connected to trigger wire 228. Trigger wire 228 moves needle pushing element 224 proximally until the needle(s) penetrates vessel wall and captured by proximal components (e.g., catcher 240 and sheath 216) outside vessel wall. The needle(s) may have parts that can detach from each other. For example, a needle body or base 222 may be held by the needle pushing element while the needle tip 226 can be detached when force is applied. The needle tip(s) with suture may be retained by capture elements outside vessel wall, such as catcher 240 and/or catcher dish 254, and detached from the needle base held by needle pushing element. The needle pushing element carrying needle base are returned to the original distal position on the device. Alternatively, needle(s) with suture may be retained and detached from the needle pushing element. The needle pushing element is returned to the original distal position on the device.

The detachment of needle tip(s) from needle base can occur prior to or simultaneously as needle pushing element is retracted. Alternatively, separation of needle(s) from needle pushing element can occur prior to or simultaneously as needle pushing element is retracted.

The needles are deployed to penetrate tissue and in turn enter catcher. The needles may be retained in the catcher by friction. Friction may be provided by various designs, components, and materials. The catcher may be stationary during needle firing or may move distally towards the needle deployment member or may move proximally towards handle. A sheath may be used to guide needle movement (or define the needle movement boundary) along the device longitudinally towards proximal end. For example, friction capture of needle may be created by variable space between sheath and catcher. Space between sheath and catcher may be wider at needle entry and narrower at needle capture.

Alternatively, space between sheath and catcher may be wider for needle entry and narrower for needle capture. In another example, the needle may be captured due to friction of interaction with material of the catcher or sheath while the space between sheath and catcher does not change longitudinally.

The needles may be captured in the catcher passively or actively. In the passive embodiment, there is no component movement or one component movement. The variable space between the sheath and the catcher may be a fixed gradient. In addition, the space between sheath and catcher may be wider at distal end and narrower at proximal end. Thus, in one embodiment, the sheath and catcher remain stationary and the needles enter into space defined by sheath and the catcher. In other words, the needles move distally and are retained by the narrowing space between sheath and the catcher. In another embodiment of the passive method, the sheath moves distally to define space for receiving the needles. The needles enter into the space defined by the sheath and the catcher and are bound/guided by the sheath inner-wall. The needles move distally and are retained by the narrowing space between the sheath and catcher. The sheath retracts proximally while the catcher remains stationary.

In the active embodiment, the space between the sheath and catcher may be a dynamic gradient. Relative motion between the sheath and catcher may change during needle movement proximally to create narrowing of inter-space between the sheath and the catcher to capture and retain the needles. The sheath and catcher may move relative to each other to create more space for needle entry into inter-space. The sheath and receiver may move relative to each other to reduce the inter-space and capture the needles. In one embodiment, the space between the sheath and catcher is opened up while the sheath moves distally to receive the needles. The space between the sheath and catcher/receiver may be reduced by retracting the sheath proximally while the catcher moves distally, or by retracting the sheath proximally while the catcher remains stationary. In another embodiment, the sheath is positioned against soft tissue. The space between the sheath and catcher may be reduced to receive the needles by moving the catcher distally.

In another embodiment, the variable space between the sheath and catcher may include mechanical engagement to enhance capture and retention of the needles more securely. The sheath may move distally to define space for receiving the needles. The needles then enter the space defined by the sheath and the catcher. The needles move distally and are retained by the narrowing space between the sheath and catcher. The retention of the needles may be enhanced by mechanical compression to engage the needles. Finally, the sheath is retracted proximally while catcher remains stationary. On skilled in the art would recognize that other methods of ensuring needle capture and retention beyond those described herein may be implemented.

Soft tissue stabilizer 214 is used to provide stabilization between soft tissue and device prior to suture deployment, minimize user effect on device during procedures. Soft tissue stabilizer has a first configuration, (closed or low profile state) to facilitate device insertion and second configuration (deployed or expanded state) to enable tissue stabilization. Soft tissue stabilizer has potential variations such as footing, loop, hook, anchor, asymmetric deflectable wings or deflectable wings and can be made of flexible or elastic metal such as metal, nitinol or polymers.

Figure 30:
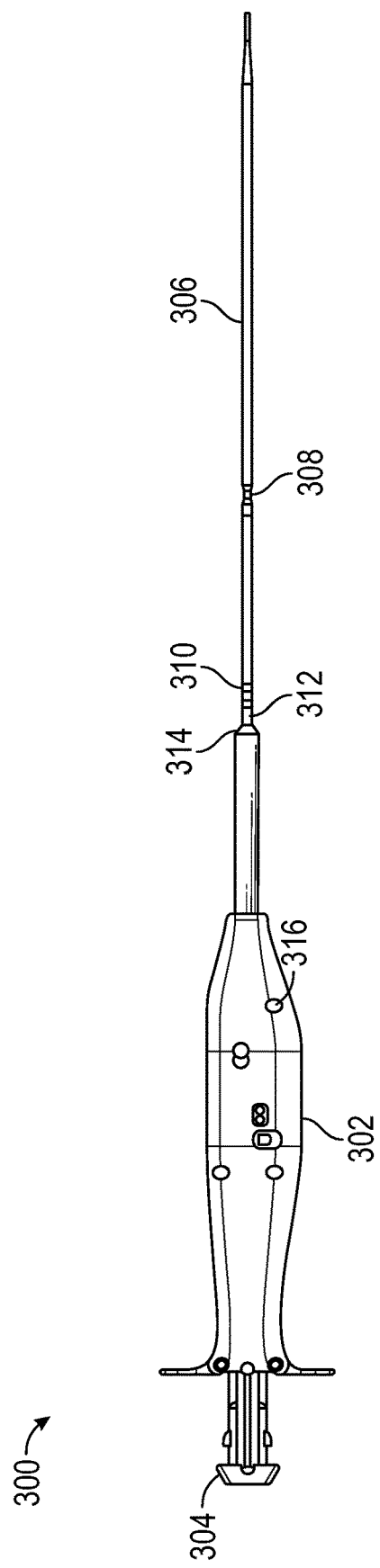
FIG. 30 schematically depicts a suture delivery device having a single actuator, according to one embodiment.

In one embodiment, the stabilizer may be omitted to allow needle deployment and suture delivery to be performed using a single actuator. For example, FIG. 30 is a schematic overview of a suture delivering device 300 including handle 302 and an actuator configured as plunger 304. The elongated distal portion of device 300 includes catheter 306 for deployment within a patient's vessel. Guidewire exchange port 308 may be used to facilitate advancement of catheter 306 over a guidewire already positioned with in the patient's vasculature using known techniques. Proximal to catheter 306 is needle deployment assembly 310. Plunger 304 may be coupled to a trigger wire (not shown in this drawing), so that proximal movement of plunger 304 results in a corresponding proximal movement of the trigger wire. The coupling may involve direct one to one movement, or may feature rack and pinion engagement or other similar mechanisms to provide a desired degree of mechanical advantage. As will be appreciated, this may include causing a first amount of travel of plunger 304 to result in a greater amount of travel of the trigger wire or causing a first amount of force applied to plunger 304 to result in a greater amount of force being applied to the trigger wire. Although described in the context of this embodiment as plunger 304, any of the actuator mechanisms described above, or any other suitable mechanism, may be employed. Needle deployment assembly 310 may be carried by a distal portion of shaft 312 as detailed below, with sheath 314 coaxially disposed over shaft 312. As shown, device 300 may include a bleed back indicator 316 on handle 302 which is in communication with a port positioned adjacent needle deployment assembly 310 to provide visual feedback in the form of blood flow when needle deployment assembly 310 is positioned within the patient's vessel.

Figure 31:
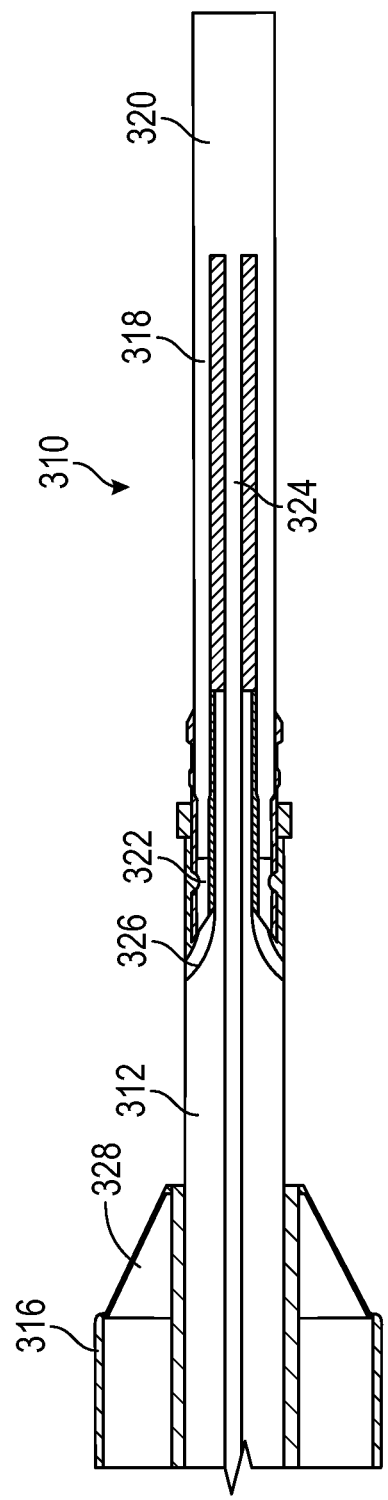
FIG. 31 schematically depicts a detail view of the needle deployment assembly of FIG. 30, according to one embodiment.

Further details regarding this embodiment are depicted in FIG. 31, which schematically shows needle deployment assembly 310, including a plurality of needle bases 318 projecting proximally from needle pushing element 320, with each needle having a detachable needle tip 322. Suture material may be threaded through or otherwise secured to an aperture in needle tip 322 (not shown in the figure for the sake of clarity). Trigger wire 324 is secured to needle pushing element 320 and extends proximally to handle 302 for actuation by plunger 304. For delivery, needle bases 318 and tips 322 are positioned distally of corresponding ramps 326 formed in shaft 312. Trigger wire 324 is slidably disposed coaxially within shaft 312 so that relative proximal movement of trigger wire 324 causes needle bases 318 and tips 322 to be deflected radially outward to a piercing angle by ramps 326. Other suitable configurations may be employed to provide the outward deflection as a result of relative proximal movement of the needles caused by trigger wire 324, including, for example, the proximal and distal rings described above. Any suitable number of needles may be employed, such as two needle base 318 and needle tip 322 sets as shown, or more. Catcher 328 is coaxially disposed within sheath 316, so that at least needle tips 322 may be engaged by one or both of catcher 328 and sheath 316 following relative proximal movement in any of the manners described herein.

Described herein are certain exemplary embodiments. However, one skilled in the art that pertains to the present embodiments will understand that the principles of this disclosure can be extended easily with appropriate modifications to other applications.

What is claimed is:

1. A suture delivery device for suturing an opening on tissue comprising:
   an elongated deployment shaft including at least one ramp;

a needle deployment assembly carried by the shaft, including a plurality of needles carrying suture material configured to have an insertion profile at a distal position and contact the at least one ramp to deflect radially outwards to a piercing angle when moved proximally relative to the shaft;

a stabilizer carried by the shaft at a location proximal of the needle deployment assembly, wherein the stabilizer is reconfigurable between an unexpanded insertion profile and an expanded profile;

a catcher tube coaxially and slidably disposed over the shaft having a catcher at a distal end, wherein the catcher is configured to retain at least a portion of each of the plurality of needles carrying the suture material when the needles are passed through the tissue to be sutured to a proximal position that engages the catcher; and a sheath coaxially and slidably disposed over the catcher tube, wherein a distal end of the sheath is configured to sandwich tissue to be sutured against the stabilizer when expanded.

2. The suture delivery device of claim 1, wherein the catcher is made of resilient material.

3. The suture delivery device of claim 1, wherein the catcher is expandable.

4. The suture delivery device of claim 1, further comprising a handle at a proximal end of the shaft, wherein the handle has a stabilizer actuator configured to expand the stabilizer.

5. The suture delivery device of claim 4, wherein the stabilizer actuator is further configured to move the sheath distally relative to the shaft.

6. The suture delivery device of claim 5, wherein the stabilizer actuator comprises a slider moveable from a proximal position to a distal position.

7. The suture delivery device of claim 6, wherein the slider is coupled to proximal ends of the sheath and the catcher tube and wherein a proximal end of the stabilizer is secured to the catcher tube and a distal end of the stabilizer is secured to the shaft such that movement of the slider from the proximal position to the distal position is configured to:

move the catcher tube distally relative to the shaft to decrease a distance between the proximal end of the stabilizer and the distal end of the stabilizer to expand the stabilizer; and move the sheath distally relative to the shaft to sandwich tissue to be sutured between the distal end of the sheath and the expanded stabilizer.

8. The suture delivery device of claim 7, wherein the handle further comprises a stabilizer control configured to automatically engage when the slider is in the distal position to prevent further relative movement between the catcher tube and the shaft and to prevent further relative movement between the sheath and the shaft.

9. The suture delivery device of claim 8, wherein the handle further comprises a release trigger configured to disengage the stabilizer control when the slider is in the distal position and allow further relative movement between the catcher tube and the shaft so that the stabilizer can return to the unexpanded insertion profile.

10. The suture delivery device of claim 7, wherein the handle has a needle actuator configured to move the needles proximally and distally relative to the shaft.

11. The suture delivery device of claim 10, wherein the needle actuator has a first range of travel configured to move the plurality of needles from the distal position to the proximal position and a second range of travel configured to move a portion of each of the plurality of needles not retained by the catcher from the proximal position to the distal position.

12. The suture delivery device of claim 11, wherein the needle actuator comprises a plunger coupled to a plunger rack, further comprising a trigger rack and a pinion, wherein the plurality of needles are coupled to the trigger rack by a trigger wire slidably and coaxially disposed within the shaft, such that during the first range of travel, the trigger rack and the plunger rack engage the pinion so that distal movement of the plunger rack causes proximal movement of the trigger wire relative to the shaft and during the second range of travel, the plunger rack does not engage the pinion and directly engages the trigger rack so that distal movement of the plunger rack causes distal movement of the trigger wire relative to the shaft.

13. The suture delivery device of claim 12, wherein the handle further comprises a stabilizer control configured to automatically engage when the slider is in the distal position to prevent further relative movement between the catcher tube and the shaft and wherein movement of the needle actuator to an end of the second range of travel disengages the stabilizer control to allow further relative movement between the catcher tube and the shaft so that the stabilizer can return to the unexpanded insertion profile.

14. The suture delivery device of claim 1, wherein the stabilizer comprises at least one deflectable wing that deflects outwards when a distance between a proximal end of the stabilizer and a distal end of the stabilizer is reduced.

15. The suture delivery device of claim 14, wherein the at least one deflectable wing has an asymmetric configuration when expanded configured to compensate for an insertion angle of the suture delivery device relative to the tissue to be sutured.

16. The suture delivery device of claim 1, further comprising a handle at a proximal end of the shaft, wherein the handle has a needle actuator configured to move the needles proximally and distally relative to the shaft.

17. The suture delivery device of claim 16, wherein the needle actuator has a first range of travel configured to move the plurality of needles from the distal position to the proximal position.

18. The suture delivery device of claim 17, wherein the needle actuator has a second range of travel configured to move a portion of each of the plurality of needles not retained by the catcher from the proximal position to the distal position.

19. The suture delivery device of claim 18, wherein the needle actuator comprises a plunger coupled to a plunger rack, further comprising a trigger rack and a pinion, wherein the plurality of needles are coupled to the trigger rack by a trigger wire slidably and coaxially disposed within the shaft, such that during the first range of travel, the trigger rack and the plunger rack engage the pinion so that distal movement of the plunger rack causes proximal movement of the trigger wire relative to the shaft.

20. The suture delivery device of claim 19, wherein during the second range of travel, the plunger rack does not engage the pinion and directly engages the trigger rack so that distal movement of the plunger rack causes distal movement of the trigger wire relative to the shaft.

21. The suture delivery device of claim 1, wherein each of the plurality of needles comprises a needle base and a detachable needle tip that carries the suture material, such that each needle tip engages the catcher when the plurality of needles are moved to the proximal position and the catcher retains each needle tip when each of the needle bases are returned to the distal position.

22. The suture delivery device of claim 21, wherein a dimension of the needle tip is different from a dimension of the needle base.

23. The suture delivery device of claim 21, wherein each needle base and corresponding needle tip is configured to have a retention force to keep the needle tips in position on the needle bases until moved proximally into engagement with the catcher.

24. The suture delivery device of claim 23, wherein the retention force depends at least in part on a surface treatment.

25. The suture delivery device of claim 24, wherein the surface treatment is a layer of nitinol oxide.

26. A method for delivering a suture comprising:
providing an elongated deployment shaft including at least one ramp, a needle deployment assembly carried by the shaft, including a plurality of needles carrying suture material, a stabilizer carried by the shaft at a location proximal of the needle deployment assembly, a catcher tube coaxially and slidably disposed over the shaft having a catcher at a distal end, and a sheath coaxially and slidably disposed over the catcher tube;
advancing the elongated deployment shaft to a desired position in a body;
reconfiguring the stabilizer from an unexpanded insertion profile to an expanded profile;
sandwiching tissue to be sutured between a distal end of the sheath and the expanded stabilizer;
deflecting the plurality of needles radially outwards to a piercing angle from an insertion profile at a distal position with proximal movement relative to the shaft to contact the at least first ramp;
engaging the catcher with the plurality of needles when moved to a proximal position by passing through the tissue to be sutured;
retaining at least a portion of each of the plurality of needles carrying the suture material with the catcher; and
returning a portion of each of the plurality of needles not retained by the needles to the insertion profile at the distal position.

27. The method of claim 26, wherein reconfiguring the stabilizer and sandwiching the tissue to be sutured is performed by operating a first actuator.

28. The method of claim 27, wherein a proximal end of the stabilizer is secured to the catcher tube and a distal end of the stabilizer is secured to the shaft, wherein operating the first actuator moves the catcher tube distally relative to the shaft to decrease a distance between the proximal end of the stabilizer and the distal end of the stabilizer to expand the stabilizer and moves the sheath distally relative to the shaft.

29. The method of claim 26, wherein deflecting the plurality of needles radially outward, engaging the catcher with the plurality of needles and returning a portion of each of the plurality of needles not retained by the catcher to the distal position is performed by operating a second actuator.

30. The method of claim 29, wherein operating the second actuator comprises moving the second actuator through a first range of travel to move the plurality of needles from the distal position to the proximal position and moving the second actuator through a second range of travel to move a portion of each of the plurality of needles not retained by the catcher from the proximal position to the distal position.

* * * * *